United States Patent
Mackie et al.

(10) Patent No.: US 12,251,248 B2
(45) Date of Patent: Mar. 18, 2025

(54) SCANNER AND METHOD OF IMAGE RECONSTRUCTION

(71) Applicant: LEO CANCER CARE, INC., Middleton, WI (US)

(72) Inventors: Thomas R. Mackie, Verona, WI (US); John Hayes, Madison, WI (US); Brent Harper, New Glarus, WI (US)

(73) Assignee: LEO CANCER CARE, INC., Middleton, WI (US)

( * ) Notice: Subject to any disclaimer, the term of this patent is extended or adjusted under 35 U.S.C. 154(b) by 149 days.

(21) Appl. No.: 17/868,967

(22) Filed: Jul. 20, 2022

(65) Prior Publication Data

US 2023/0038970 A1 Feb. 9, 2023

Related U.S. Application Data

(60) Provisional application No. 63/244,496, filed on Sep. 15, 2021, provisional application No. 63/224,460, filed on Jul. 22, 2021.

(51) Int. Cl.
| | |
|---|---|
| *A61B 6/40* | (2024.01) |
| *A61B 6/00* | (2006.01) |
| *A61B 6/03* | (2006.01) |
| *A61B 6/42* | (2024.01) |
| *G06T 11/00* | (2006.01) |

(52) U.S. Cl.
CPC ............ *A61B 6/035* (2013.01); *A61B 6/4035* (2013.01); *A61B 6/4266* (2013.01); *A61B 6/4447* (2013.01); *A61B 6/4452* (2013.01); *A61B 6/482* (2013.01); *A61B 6/5205* (2013.01); *G06T 11/005* (2013.01); *G06T 11/006* (2013.01); *A61B 6/4078* (2013.01); *G06T 2211/408* (2013.01); *G06T 2211/416* (2013.01); *G06T 2211/424* (2013.01)

(58) Field of Classification Search
CPC ..... A61B 6/035; A61B 6/4035; A61B 6/4266; A61B 6/4452; A61B 6/4078; A61B 6/032; A61B 6/4208; A61B 6/4447; G06T 11/005; G06T 2211/408; G06T 11/006
See application file for complete search history.

(56) References Cited

U.S. PATENT DOCUMENTS

| | | | |
|---|---|---|---|
| 7,466,792 B2 | 12/2008 | Bakai et al. | |
| 8,712,012 B2 | 4/2014 | O'connor | |

(Continued)

FOREIGN PATENT DOCUMENTS

WO WO 2019/056055 3/2019

OTHER PUBLICATIONS

Boisbouvier, S. et al. Upright patient positioning for pelvic radiotherapy treatments. Tech Innov Patient Support Radiat Oncol. Nov. 28, 2022;24:124-130.

(Continued)

*Primary Examiner* — Dani Fox
*Assistant Examiner* — Mamadou Faye
(74) *Attorney, Agent, or Firm* — Brian F. Bradley; Thomas A. Isenbarger; Casimir Jones, S.C.

(57) ABSTRACT

Provided herein is technology relating to radiology and radiotherapy and particularly, but not exclusively, to apparatuses, methods, and systems for multi-axis medical imaging of patients in vertical and horizontal positions with single or dual energy acquisition.

24 Claims, 18 Drawing Sheets

(56) References Cited

U.S. PATENT DOCUMENTS

| | | | |
|---|---|---|---|
| 2007/0147581 A1 | 6/2007 | Ellenbogen et al. | |
| 2010/0322498 A1 | 12/2010 | Wieczorek et al. | |
| 2013/0064344 A1 | 3/2013 | Carol | |
| 2014/0139215 A1 | 5/2014 | Gregerson et al. | |
| 2014/0153690 A1* | 6/2014 | Claus | A61B 6/027 378/19 |
| 2014/0254747 A1* | 9/2014 | Saito | G21K 1/10 378/5 |
| 2014/0314200 A1 | 10/2014 | Chen et al. | |
| 2015/0173696 A1* | 6/2015 | Zingerman | A61B 6/4417 378/9 |
| 2018/0310899 A1* | 11/2018 | Garlow | A61B 6/5205 |
| 2020/0101324 A1* | 4/2020 | Sharpless | A61N 5/103 |
| 2020/0196972 A1* | 6/2020 | Zhou | G06N 3/045 |
| 2020/0268327 A1 | 8/2020 | Feain et al. | |
| 2022/0183641 A1 | 6/2022 | Harper et al. | |

OTHER PUBLICATIONS

Crawford C.R. et al., Computed tomography scanning with simultaneous patient translation, Med. Phys. 1990; 17: 967-982.

Eslick E.M. et al. The Nano-X Linear Accelerator: A Compact and Economical Cancer Radiotherapy System Incorporating Patient Rotation. Technol Cancer Res Treat. Oct. 2015;14(5):565-72.

Feldkamp, L.A., Practical Cone-Beam Algorithm, Journal of the Optical Society of America, 1984; 1: 612-619.

Jinzaki, M. et al. Development of Upright Computed Tomography With Area Detector for Whole-Body Scans: Phantom Study, Efficacy on Workflow, Effect of Gravity on Human Body, and Potential Clinical Impact. Invest Radiol. Feb. 2020;55(2):73-83.

Kak, A.C., Principles of Computerized Tomographic Imaging, 2001. Table of contents.

Parker, D L, Optimal short scan convolution reconstruction for fanbeam CT, Medical Physics, 1982; 9:254-257.

Schreuder, N. et al. Fixed beamlines can replace gantries for particle therapy. Med Phys. Apr. 2022;49(4):2097-2100.

Tuy, HK. An inversion formula for cone-beam reconstruction. SIAM J Appl Math. 1983; 43: 546-52.

Yamada, Y. et al. Differences in Lung and Lobe vols. between Supine and Standing Positions Scanned with Conventional and Newly Developed 320-Detector-Row Upright CT: Intra-Individual Comparison. Respiration. 2020;99(7):598-605.

International Search Report and Written Opinion for PCT/US2022/037662, mailed Nov. 22, 2022, 14 pages.

* cited by examiner

LCC detector:
--oriented to source
--centered on rotation axis

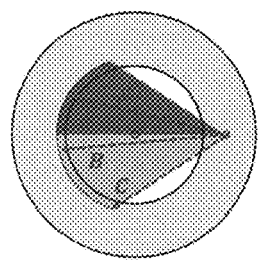 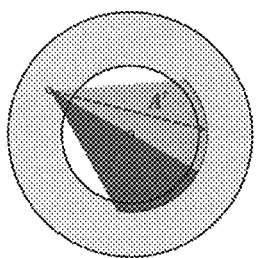 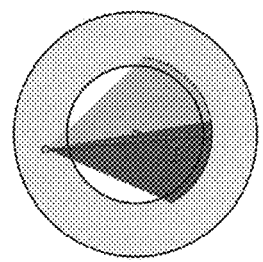 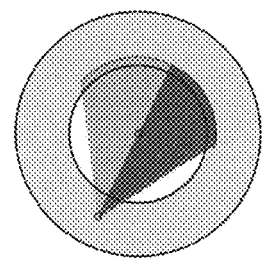
FIG. 16A     FIG. 16B     FIG. 16C     FIG. 16D
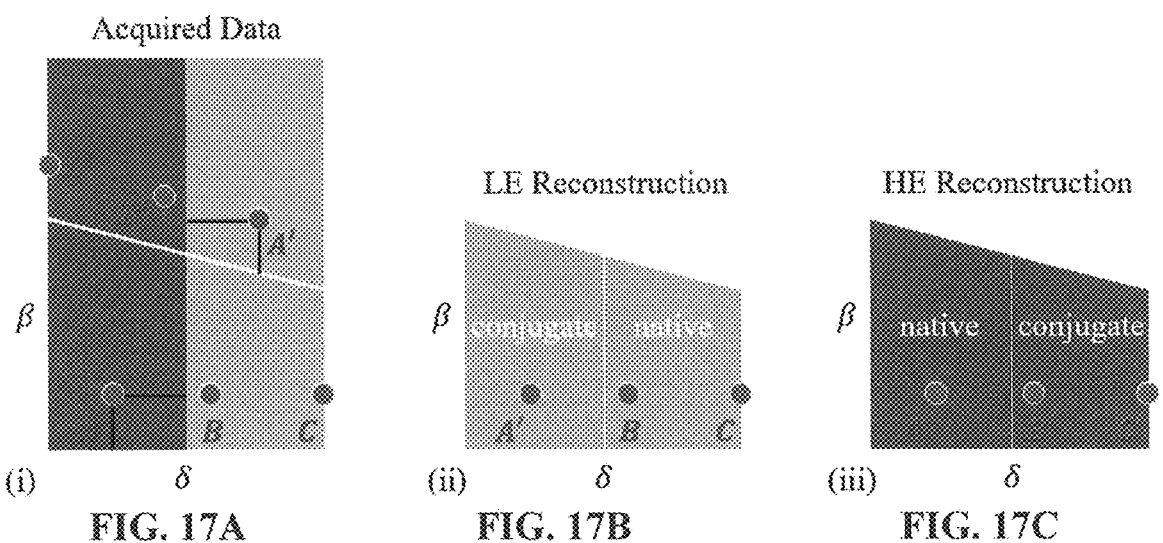
FIG. 17A     FIG. 17B     FIG. 17C
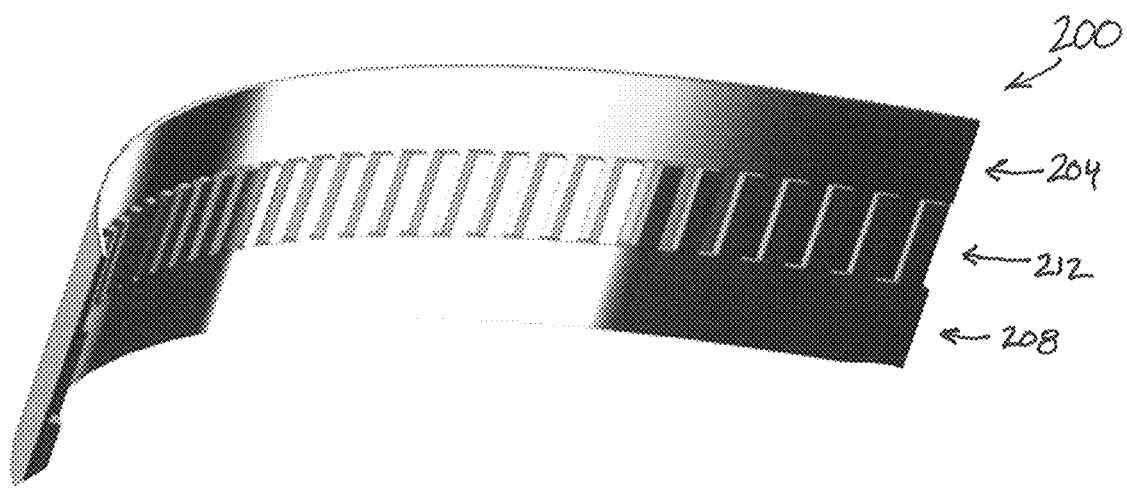
FIG. 18

Low Energy (LE = 65 kV) Sinogram
High Energy (HE = 85 kV) Sinogram
Dual Energy (DECT) Sinogram
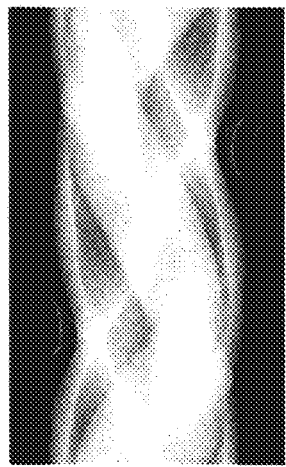
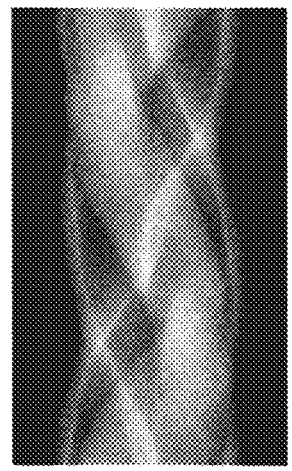
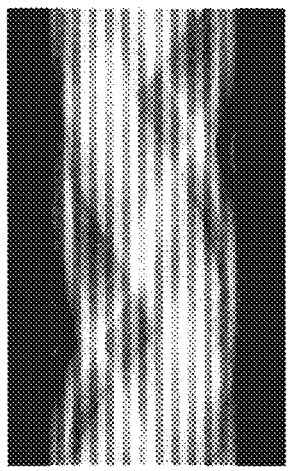
17 LE bands + 17 HE bands (32 columns/filter band)
FIG. 23A          FIG. 23B          FIG. 23C
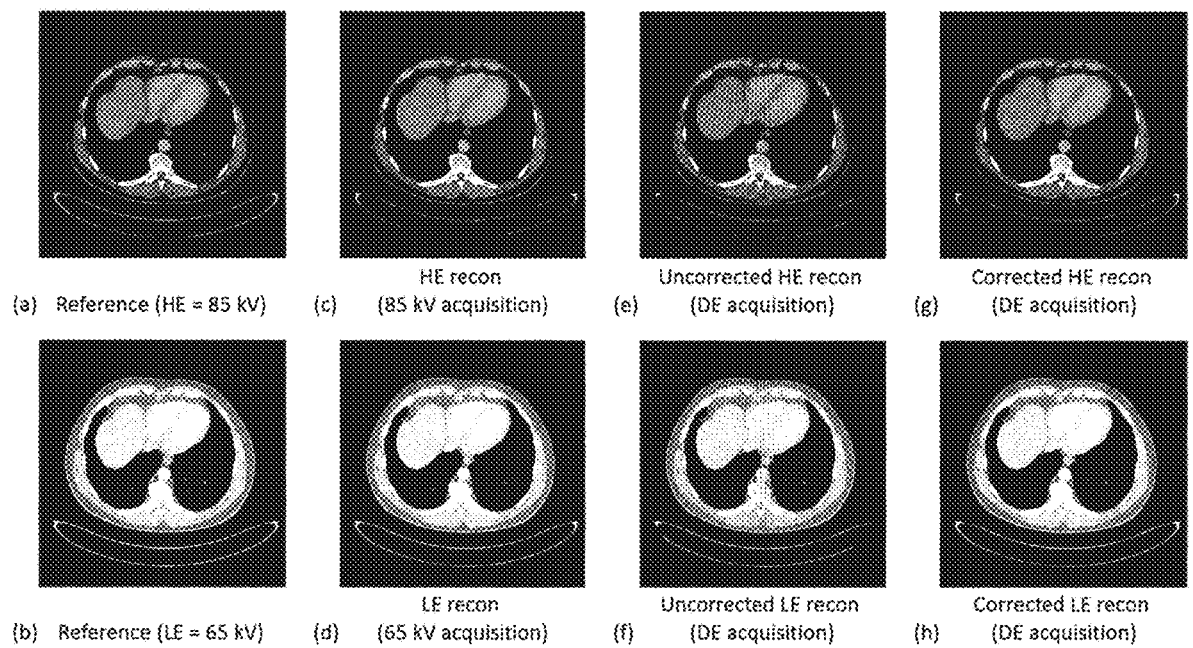
FIG. 24

| | |
|---|---|
| r1c16 t7 | spatially advanced 7 elements, data taken in the same column location at 7 time samples earlier |
| r1c16 t7 | spatially advanced 7 elements, data taken in the same column location at 7 time samples earlier |
| r1c15 t8 | spatially advanced 6 elements, data taken in the same column location at 6 time samples earlier |
| r1c15 t8 | spatially advanced 6 elements, data taken in the same column location at 6 time samples earlier |
| r1c14 t9 | spatially advanced 5 elements, data taken in the same column location at 5 time samples earlier |
| r1c14 t9 | spatially advanced 5 elements, data taken in the same column location at 5 time samples earlier |
| r1c13 t10 | spatially advanced 4 elements, data taken in the same column location at 4 time samples earlier |
| r1c13 t10 | spatially advanced 4 elements, data taken in the same column location at 4 time samples earlier |
| r1c12 t11 | spatially advanced 3 elements, data taken in the same column location at 3 time samples earlier |
| r1c12 t11 | spatially advanced 3 elements, data taken in the same column location at 3 time samples earlier |
| | spatially advanced 2 elements, data taken in the same column location at 2 time samples earlier |
| | spatially advanced 2 elements, data taken in the same column location at 2 time samples earlier |
| | spatially advanced 1 element, data taken in the same column location at 1 time sample earlier |
| | spatially advanced 1 element, data taken in the same column location at 1 time sample earlier |
| r1c9 t14 | Traditional pixel element used for reconstruction |
| r1c9 t14 | Traditional pixel element used for reconstruction |
| | spatially trailing 1 element, data taken in the same column location at 1 time sample later |
| | spatially trailing 1 element, data taken in the same column location at 1 time sample later |
| | spatially trailing 2 elements, data taken in the same column location at 2 time samples later |
| | spatially trailing 2 elements, data taken in the same column location at 2 time samples later |
| r1c6 t17 | spatially trailing 3 elements, data taken in the same column location at 3 time samples later |
| r1c6 t17 | spatially trailing 3 elements, data taken in the same column location at 3 time samples later |
| r1c5 t18 | spatially trailing 4 elements, data taken in the same column location at 4 time samples later |
| r1c5 t18 | spatially trailing 4 elements, data taken in the same column location at 4 time samples later |
| r1c4 t19 | spatially trailing 5 elements, data taken in the same column location at 5 time samples later |
| r1c4 t19 | spatially trailing 5 elements, data taken in the same column location at 5 time samples later |
| r1c3 t20 | spatially trailing 6 elements, data taken in the same column location at 6 time samples later |
| r1c3 t20 | spatially trailing 6 elements, data taken in the same column location at 6 time samples later |
| r1c2 t21 | spatially trailing 7 elements, data taken in the same column location at 7 time samples later |
| r1c2 t21 | spatially trailing 7 elements, data taken in the same column location at 7 time samples later |

FIG. 27

SCANNER AND METHOD OF IMAGE RECONSTRUCTION

STATEMENT OF RELATED APPLICATIONS

This application claims priority to U.S. Provisional Patent Application No. 63/224,460, filed Jul. 22, 2021, and to U.S. Provisional Patent Application No. 63/244,496, filed Sep. 15, 2021, the entire contents of which are incorporated herein by reference for all purposes.

FIELD

Provided herein is technology relating to radiology and radiotherapy and particularly, but not exclusively, to apparatuses, methods, and systems for medical imaging and image reconstruction.

BACKGROUND

Medical imaging is used to diagnose, stage, plan treatment, guide treatment, and evaluate response to treatment in patients for numerous types of diseases, injuries, and other maladies. In particular, computerized tomography (CT) is a form of medical imaging that produces a three-dimensional model of an object (e.g., a patient or portion thereof) using multiple two-dimensional X-ray measurements taken from different angles. CT imaging produces tomographic (cross-sectional) images of targeted areas of a patient or portion thereof, thus allowing a user to image the interior of the patient without cutting the patient. In conventional CT, a patient is placed horizontally on a couch or gurney and the patient and couch are moved into the CT scanning apparatus. Alternatively, gurneys may be fixed and the CT scanner moves horizontally. New technologies are needed to allow imaging of patients safely in multiple positions, e.g., vertical and/or essentially vertical positions (e.g., standing, sitting, kneeling, etc.) in addition to horizontal positions and/or essentially horizontal positions (e.g., lying (e.g., prone or supine)) and other patient positions such as tilted forwards or backwards and other orthopedic positions. New technologies are also needed to allow image reconstruction for both single energy and simultaneous dual energy acquisition for such CT scanners.

SUMMARY

The technology described herein relates to medical imaging, e.g., computerized tomography (CT), magnetic resonance imaging (MRI), positron emission tomography (PET), single-photon emission computerized tomography (SPECT), photon counting computed tomography, portal imaging (e.g., prior to a treatment), radiograph localizers, topograms or scanned projection radiography ("scout view") (e.g., prior to an imaging scan and/or prior to a treatment).

Dual energy CT (DECT) can produce a wide variety of patient images that are useful in clinical radiology as an alternative or supplemental to single energy CT. For example, a dual energy CT scanner can produce a pair of images (X-ray attenuation maps) at both low and high energies. Additionally, dual energy CT scanners are capable of creating virtual monoenergetic, effective atomic number, electron density, material specific, and virtual non-contrast images, among other image types, which have uses in both radiology and radiotherapy applications. For example, in radiotherapy, the effective atomic number and electron density images can be used to calculate the stopping power for charged particles used in particle therapy. As such, a proton stopping power image can be used in treatment planning systems for proton beam therapy. In addition, in radiology, a dual energy CT scanner provides valuable information to clinicians for the diagnosis of pathologies in the abdomen, kidney, liver, and lungs. Also, dual energy CT scanners are helpful in material identification of gout, calcium, and iodinated contrast and for the separation of these materials from bone and other bodily materials. In some instances, a dual energy CT scanner can provide the same quality image as single energy CT, while reducing dose to the patient. In short, a dual energy CT scanner provides clinical benefits, for example, by providing more diagnostic information than a single energy CT scanner for the same dose.

Conventional dual energy CT scanners utilize sequential scans separated in time by at least one rotation of the same object performed at different kV levels. Variations of conventional dual energy CT include temporally varying the X-ray source energy, using multiple X-ray tubes, using energy resolving detectors, and filtering the X-ray beam in a row direction either at the detector or at the source. The quality of dual energy CT images depends on, among other things, the spatial, temporal, contrast, and energy resolution of the acquisition system and reconstruction algorithm. Conventional dual energy CT scanners need improvement in the spatial registration and temporal resolution of the two images produced at the two different energy spectra. In particular, the spectral separation of the low and high energy acquisitions is desirable so that higher contrast and material separation in the images can be provided. Some conventional dual energy CT scanners have disadvantages (e.g., bad temporal registration, prone to motion artifacts, limited spectral separation, high noise on low kV image; and/or are expensive, slow, large, or submit patients to a higher dose). For example, systems with multiple tubes can provide good spatial and temporal resolution but come with a high cost and complexity.

The technology provided herein relates to a dual energy CT scanner and associated image acquisition and reconstruction technology that increases spatial and temporal resolution over conventional dual energy CT scanner designs. A dual energy filter positioned at the source as disclosed herein includes alternating materials that attenuate the X-ray source to different levels, thereby providing spectral separation. As such, the object to be imaged by X-ray beams is probed by both a low and a high energy spectrum. The X-ray spectra at the source is divided along the detector channel direction (a columns direction). Two energy spectra pass through an object and are measured simultaneously, and a controller parses the low and high energy signals into complete data sets that can be reconstructed into two separate low and high energy images.

The disclosure provides, in one aspect, a computerized tomography (CT) scanner including a source positioned a first distance from a center, wherein the source is rotatable about the center, and a plurality of detectors rotatable about the center. The plurality of detectors are positioned at a plurality of distances from the source. In some embodiments, the center is a rotational axis.

In some embodiments, each of the plurality of detectors is positioned a second distance from the center.

In some embodiments, the first distance is larger than second distance.

In some embodiments, each of the plurality of detectors is oriented to the source.

In some embodiments, each of the plurality of detectors includes a detector face defining an input plane, and wherein the input plane is orthogonal to an incident beam from the source.

In some embodiments, each of the plurality of detectors is oriented to the center.

In some embodiments, each of the plurality of detectors is oriented with an edge aligned with an edge of an adjacent detector.

In some embodiments, the plurality of detectors define a field of view of at least 50 centimeters (e.g., 50, 55, 60, 65, 70, 75, 80, 85, 90, etc. centimeters).

In some embodiments, the variance of photon fluence among the plurality of detectors is less than 50% (e.g., less than 50%, 45%, 40%, 35%, 30%, 25%, 20%, 15%, 10%, or 5%).

In some embodiments, the CT scanner is movable between an upright configuration, a tilted configuration, and a horizontal configuration.

The disclosure provides, in another aspect, a computerized tomography (CT) scanner including a source defining an imaging plane and a filter. The filter includes a first filter portion with a first material and/or profile, a second filter portion with a second material and/or profile, and a third filter portion with the first material and the second material, which can also include a profile (e.g., a bowtie profile). The filter is movable with respect to the source to align any one of the first filter portion, the second filter portion, and the third filter portion with the imaging plane.

In some embodiments, the third filter portion includes alternating columns of the first material and the second material, wherein each column intersects the imaging plane.

In some embodiments, the first material attenuates an X-ray spectrum a first amount, and the second material attenuates the X-ray spectrum a second amount, different than the first amount.

In some embodiments, the first material has a first mass attenuation coefficient within a range of 0.1 $cm^2/g$ to 200 $cm^2/g$ (e.g., 0.1, 0.5, 1, 5, 10, 50, 100, 150, 200) corresponding to an excitation within a range of 10 to 200 kVp (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200), and the second material has a second mass attenuation coefficient corresponding to the excitation different than the first mass attenuation coefficient. The two materials, in some embodiments, have different energy curves over the range of $kV_p$. In some embodiments, the first mass attenuation coefficient is different than the second mass attenuation coefficient by at least one order of magnitude for a given excitation. In some embodiments, the first material is gold, and wherein the second material is molybdenum. In some embodiments, the first material is gold, and wherein the second material is tin.

In some embodiments, the third filter portion is positioned between the first filter portion and the second filter portion.

In some embodiments, the filter defines a radius.

In some embodiments, a filter adjustment assembly includes a motor, a frame, and a linkage coupled between the motor and the frame. In some embodiments, the filter is coupled to the frame.

In some embodiments, the first filter portion at least partially overlaps the third filter portion, and the second filter portion at least partially overlaps the third filter portion.

The disclosure provides, in another aspect, a method of creating a CT image including rotating a source and at least one detector about an axis. The at least one detector is configured to detect an output from the source. The method also includes recording an output signal from the at least one detector as sampled data, separating the sampled data into a first data set and a second data set, completing the first data set with a data completion module to create a first full data set, and completing the second data set with the data completion module to create a second full data set. The method also includes reconstructing a first CT image with the full first data set and reconstructing a second CT image with the full second data set.

In some embodiments, the data completion module utilizes conjugate data.

In some embodiments, the data completion module utilizes a high order interpolation.

In some embodiments, the data completion module utilizes a machine learning method.

In some embodiments, the method further includes iterating on reconstructing the first CT image and/or the second CT image.

In some embodiments, the source and the at least one detector translate along the axis while rotating about the axis.

In some embodiments, the method further includes transforming the first data set from a first geometric frame of reference to a second geometric frame of reference.

Additional embodiments will be apparent to persons skilled in the relevant art based on the teachings contained herein.

BRIEF DESCRIPTION OF THE DRAWINGS

FIG. 16A illustrates three X-ray samples (A, B, C) with the source in a first position, with sample A acquired at a high energy and sample B and C acquired at a low energy.

FIG. 16B illustrates the conjugate ray to sample A as sample A', which is acquired at low energy, and with the source in a second position.

FIG. 16C illustrates the conjugate ray to sample B as sample B', which is acquired at high energy, and with the source in a third position.

FIG. 16D illustrates the conjugate ray to sample C as sample C', which is acquired at high energy, and with the source in a fourth position.

FIG. 17A is a sinogram of samples A, A', B, B', C, and C' of FIGS. 16A-16D.

FIG. 17B is a sinogram for low energy reconstruction including both native and conjugate samples.

FIG. 17C is a sinogram for high energy reconstruction including both native and conjugate samples.

FIG. 18 is a perspective view of an assembly with a low-energy filter, a radial dual-energy filter, and a high-energy filter.

FIG. 23A is a low energy sinogram.

FIG. 23B is a high energy sinogram.

FIG. 23C is a dual energy sinogram.

FIG. 24 is a series of images with (a-b) being references used for simulation, (c-d) are the high and low energy acquisition reconstruction, (e-h) are the dual energy acquisition reconstructions using conjugate data filing.

FIG. 27 is a high order interpolation data completion scheme.

Figure 1:
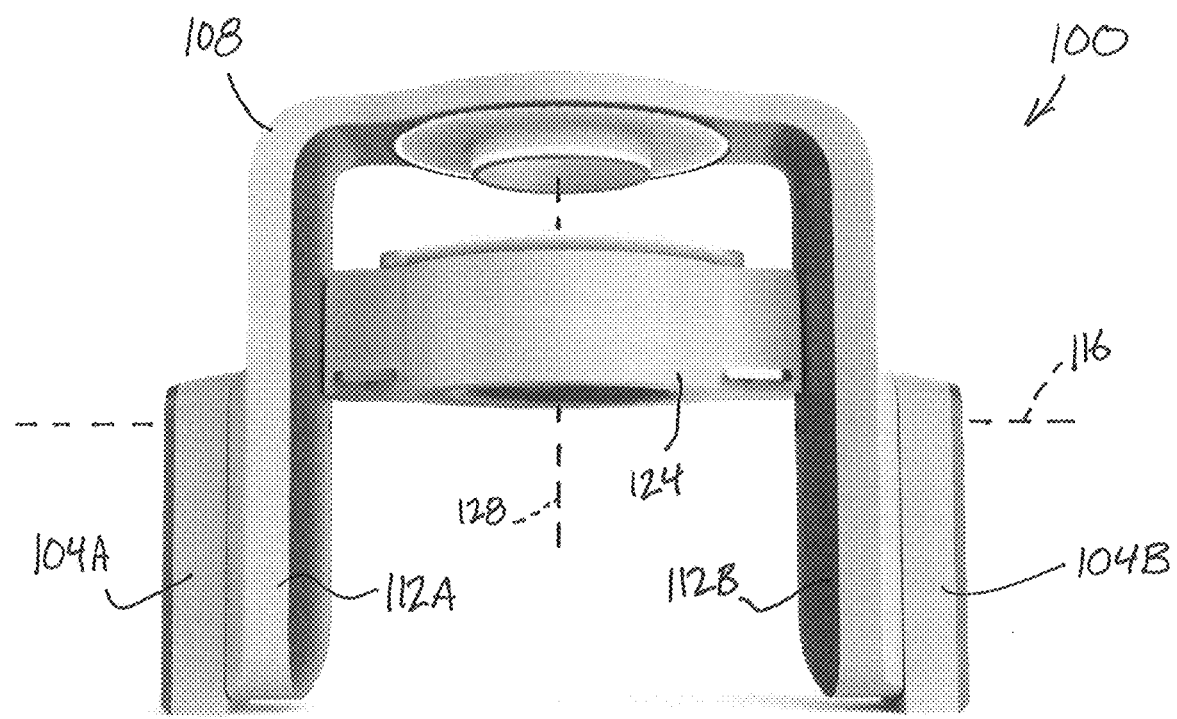
FIG. 1 a front view of a multi-axis CT scanner.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to medical imaging and particularly, but not exclusively, to apparatuses, methods, and systems for radiology (e.g., using computerized tomography) and radiotherapy.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling, performing, and/or directing methods.

As used herein, the term "computed tomography" is abbreviated "CT" and refers both to tomographic and non-tomographic radiography. For instance, the term "CT" refers to numerous forms of CT, including but not limited to X-ray CT, positron emission tomography (PET), single-photon emission computed tomography (SPECT), and photon counting computed tomography. Generally, computed tomography (CT) comprises use of an X-ray source and a detector that rotates around a patient and subsequent reconstruction of images into different planes. Currents for X-rays used in CT describe the current flow from a cathode to an anode and are typically measured in milliamperes (mA).

As used herein, the term "structured to [verb]" means that the identified element or assembly has a structure that is shaped, sized, disposed, coupled, and/or configured to perform the identified verb. For example, a member that is "structured to move" is movably coupled to another element and includes elements that cause the member to move or the member is otherwise configured to move in response to other elements or assemblies. As such, as used herein, "structured to [verb]" recites structure and not function. Further, as used herein, "structured to [verb]" means that the identified element or assembly is intended to, and is designed to, perform the identified verb.

As used herein, the term "associated" means that the elements are part of the same assembly and/or operate together or act upon/with each other in some manner. For example, an automobile has four tires and four hub caps. While all the elements are coupled as part of the automobile, it is understood that each hubcap is "associated" with a specific tire.

As used herein, the term "coupled" refers to two or more components that are secured, by any suitable means, together. Accordingly, in some embodiments, the statement that two or more parts or components are "coupled" shall mean that the parts are joined or operate together either directly or indirectly, e.g., through one or more intermediate parts or components. As used herein, "directly coupled" means that two elements are directly in contact with each other. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof. Further, an object resting on another object held in place only by gravity is not "coupled" to the lower object unless the upper object is otherwise maintained substantially in place. That is, for example, a book on a table is not coupled thereto, but a book glued to a table is coupled thereto.

As used herein, the term "removably coupled" or "temporarily coupled" means that one component is coupled with another component in an essentially temporary manner. That is, the two components are coupled in such a way that the joining or separation of the components is easy and does not damage the components. Accordingly, "removably coupled" components may be readily uncoupled and recoupled without damage to the components.

As used herein, the term "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, the term "rotatably coupled" refers to two or more components that are coupled in a manner such that at least one of the components is rotatable with respect to the other.

As used herein, the term "translatably coupled" refers to two or more components that are coupled in a manner such that at least one of the components is translatable with respect to the other.

As used herein, the term "temporarily disposed" means that a first element or assembly is resting on a second element or assembly in a manner that allows the first element/assembly to be moved without having to decouple or otherwise manipulate the first element. For example, a book simply resting on a table, e.g., the book is not glued or fastened to the table, is "temporarily disposed" on the table.

As used herein, the term "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, a "path of travel" or "path," when used in association with an element that moves, includes the space an element moves through when in motion. As such, any element that moves inherently has a "path of travel" or "path."

As used herein, the statement that two or more parts or components "engage" one another shall mean that the elements exert a force or bias against one another either directly or through one or more intermediate elements or components. Further, as used herein with regard to moving parts, a moving part may "engage" another element during the motion from one position to another and/or may "engage" another element once in the described position. Thus, it is understood that the statements, "when element A moves to element A first position, element A engages element B," and "when element A is in element A first position, element A engages element B" are equivalent statements and mean that element A either engages element B while moving to element A first position and/or element A either engages element B while in element A first position.

As used herein, the term "operatively engage" means "engage and move." That is, "operatively engage" when used in relation to a first component that is structured to move a movable or rotatable second component means that the first component applies a force sufficient to cause the second component to move. For example, a screwdriver may be placed into contact with a screw. When no force is applied to the screwdriver, the screwdriver is merely "coupled" to the screw. If an axial force is applied to the screwdriver, the screwdriver is pressed against the screw and "engages" the screw. However, when a rotational force is applied to the screwdriver, the screwdriver "operatively engages" the screw and causes the screw to rotate. Further, with electronic components, "operatively engage" means that one component controls another component by a control signal or current.

As used herein, the term "number" shall mean one or an integer greater than one (e.g., a plurality).

As used herein, in the phrase "[x] moves between its first position and second position," or, "[y] is structured to move [x] between its first position and second position," "[x]" is the name of an element or assembly. Further, when [x] is an element or assembly that moves between a number of positions, the pronoun "its" means "[x]," i.e., the named element or assembly that precedes the pronoun "its."

As used herein, a "radial side/surface" for a circular or cylindrical body is a side/surface that extends about, or encircles, the center thereof or a height line passing through the center thereof. As used herein, an "axial side/surface" for a circular or cylindrical body is a side that extends in a plane extending generally perpendicular to a height line passing through the center. That is, generally, for a cylindrical soup can, the "radial side/surface" is the generally circular sidewall and the "axial side(s)/surface(s)" are the top and bottom of the soup can.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. For instance, the term "subject" or "patient" refers to organisms including, but not limited to, humans and veterinary animals (dogs, cats, horses, pigs, cattle, sheep, goats, and the like). In the context of the technology, the term "subject" or "patient" generally refers to an individual who will be subject to a CT scan to diagnose a disease or injury; and/or to prepare for a treatment.

As used herein, a "diagnostic" test includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject having a cancer or the likelihood that such a subject will respond favorably to a compound (e.g., a pharmaceutical, e.g., a drug) or other treatment.

As used herein, the term "condition" refers generally to a disease, malady, injury, event, or change in health status.

As used herein, the term "treating" or "treatment" with respect to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. In some embodiments, "treatment" comprises exposing a patient or a portion thereof (e.g., a tissue, organ, body part, or other localize region of a patient body) to radiation (e.g., electromagnetic radiation, ionizing radiation).

The term "network" as used herein generally refers to any suitable electronic network including, but not limited to, a wide area network ("WAN") (e.g., a TCP/IP based network), a local area network ("LAN"), a neighborhood area network ("NAN"), a home area network ("HAN"), or personal area network ("PAN") employing any of a variety of communications protocols, such as Wi-Fi, Bluetooth, ZigBee, etc. In some embodiments, the network is a cellular network, such as, for example, a Global System for Mobile Communications ("GSM") network, a General Packet Radio Service ("GPRS") network, an Evolution-Data Optimized ("EV-DO") network, an Enhanced Data Rates for GSM Evolution ("EDGE") network, a 3GSM network, a 4GSM network, a 5G New Radio, a Digital Enhanced Cordless Telecommunications ("DECT") network, a digital AMPS ("IS-136/TDMA") network, or an Integrated Digital Enhanced Network ("iDEN") network, etc.

The term "computer" as used herein generally includes a plurality of electrical and electronic components that provide power, operational control, and protection to the components and modules within the system. For example, a computer can include, among other things, a processing unit (e.g., a microprocessor, a microcontroller, or other suitable programmable device), a memory, input units, and output units. The processing unit can include, among other things, a control unit, an arithmetic logic unit ("ALC"), and a plurality of registers, and can be implemented using a known computer architecture (e.g., a modified Harvard architecture, a von Neumann architecture, etc.). A "microprocessor" or "processor" refers to one or more microprocessors that can be configured to communicate in a stand-alone and/or a distributed environment, and can be configured to communicate via wired or wireless communications with other processors, where such one or more processor can be configured to operate on one or more processor-controlled devices that can be similar or different devices.

The term "memory" as used herein generally refers to any memory storage of the computer and is a non-transitory computer readable medium. The memory can include, for example, a program storage area and the data storage area. The program storage area and the data storage area can include combinations of different types of memory, such as a ROM, a RAM (e.g., DRAM, SDRAM, etc.), EEPROM, flash memory, a hard disk, a SD card, or other suitable magnetic, optical, physical, or electronic memory devices. The processing unit can be connected to the memory and execute software instructions that are capable of being stored in a RAM of the memory (e.g., during execution), a ROM of the memory (e.g., on a generally permanent bases), or another non-transitory computer readable medium such as another memory or a disc. "Memory" can include one or more processor-readable and accessible memory elements and/or components that can be internal to the processor-controlled device, external to the processor-controlled device, and can be accessed via a wired or wireless network. Software included in the implementation of the methods disclosed herein can be stored in the memory. The software includes, for example, firmware, one or more applications, program data, filters, rules, one or more program modules, and other executable instructions. For example, the computer can be configured to retrieve from the memory and execute, among other things, instructions related to the processes and methods described herein.

The term "conjugate" as used herein generally refers to a sample that has a reciprocal relation with another sample. A conjugate sample can include a sample measured with through the same cross-section of the subject as another sample. In a preferred embodiment, a first sample is acquired with the source and detectors in a first orientation and the conjugate sample is acquired with the source and detectors in a second orientation that is the mirrored first orientation.

Description

The technology provided herein relates to a medical imaging apparatus. While described in some embodiments for computed tomography (CT), the technology is not limited to use with CT and finds use for other medical imaging technologies such as, e.g., radiography, fluoroscopy, MRI, SPECT, PET, photon counting computed tomography, and portal imaging (e.g., prior to a treatment) or scanned projection radiography. Computed tomography (CT), and in particular computer X-ray tomography, is an imaging technique that generates cross-sectional images of a patient by mathematically combining multiple X-ray images (projections) taken along the plane of the cross-section at a range of angles. In conventional CT, generating a tomographic image involves providing a projection set of multiple projections over at least 180 degrees and preferably 360 degrees of angular range about the patient. The patient is typically moved through a gantry holding an X-ray source and X-ray detector that turn in coordinated opposition about the patient to acquire each X-ray projection set, either continuously during the orbital motion (helical scanning) or step-wise in between orbits (step scanning) to obtain X-ray projection sets for adjacent cross-sectional images that together describe a volume of tissue. Movement of the patient is conventional CT is provided by supporting a horizontal patient on a horizontally extending radio translucent table that is moved through the gantry.

CT imaging of some patients may preferably be performed with the patient in a vertical position (e.g., a sitting, kneeling, standing, and/or reclining position (e.g., seated, seated and leaning backward, seated and leaning forward, standing, standing and leaning backward, standing and leaning forward, kneeling, kneeling and leaning forward, or kneeling and leaning backward)). For example, a lung cancer patient undergoing thoracic radiotherapy may prefer to be in a standing position so as not to promote the coughing that often accompanies this treatment. Some medical conditions such as vertebral fractures may be more evident in a weight-bearing standing position. Accordingly, CT scanners that record CT scans of patients in a vertical position would benefit medical diagnosis and treatment. Further, a CT scanner that is capable of scanning on multiple axes, e.g., to scan patients in a vertical position, patients positioned in a conventional horizontal position, and in other positions, would expand the use scenarios of the CT scanner to address more diseases, injuries, and maladies, and to improve the cost effectiveness of the CT scanner.

As described herein, dual energy CT image acquisition is provided using a physical filter positioned at the source that includes alternating material windows (e.g., gold (Au) and molybdenum (Mo)) that filters the X-ray energy spectrum along the detector channel direction (column direction). In other words, the two materials in the filter provide different energy spectra to inspect the object with. The frequency of alternating the low and high energy signals is a free parameter of the design disclosed herein. In other words, the design with N detector channels may alternate energy levels ever M channels resulting N/M filtration windows. In some embodiments, the alternating windows are oriented radially.

Reconstruction of two images from the alternating discontinuous signal measure by the detectors is provided by a data completion module to provide a full continuous signal for each energy level. As discussed further herein, the data completion module, in some embodiments, includes a conjugate data filling scheme, a high order interpolation, and/or machine learning. Images are also formed from sparse iterative reconstruction using only the native discontinuous signals as an input to the iterative reconstruction. The systems and methods described herein improve the spatial, temporal, and energy resolution of dual energy CT images.

Apparatus

In some embodiments, the technology relates to a multi-axis medical imaging apparatus. In some embodiments, the medical imaging apparatus is a computerized tomography (CT) apparatus, a magnetic resonance imaging (MRI) apparatus, a positron emission tomography (PET) apparatus, a single-photon emission computerized tomography (SPECT) apparatus, a photon counting computed tomography apparatus, or a portal imaging or scan projection radiography apparatus. While the technology is described for exemplary embodiments wherein the medical imaging apparatus is a computerized tomography (CT) apparatus, the technology is not limited to a CT scanning apparatus and embodiments are to be understood to include other types of medical imaging apparatuses, methods, and systems.

In some embodiments, e.g., as shown in FIG. 1, the technology provides a multi-axis CT scanner 100 comprising stanchions (e.g., a first stanchion 104A and/or a second stanchion 104B). In some embodiments, the multi-axis CT scanner 100 is as described in U.S. Provisional Pat. App. No. 63/121,304 filed Dec. 4, 2020, which is incorporated herein by reference. In some embodiments, the stanchions are mounted into the floor of a room in which the multi-axis CT scanner is located. Further, in some embodiments, the multi-axis CT scanner 100 comprises a gantry 108 (e.g., a "U-shaped" gantry). In some embodiments, the gantry 108 comprises a first gantry arm 112A and a second gantry arm 112B. In some embodiments, the gantry 108 rotates around an axis (e.g., axis 116) relative to the first stanchion 104A and the second stanchion 104B, e.g., the first gantry arm 112A and the second gantry arm 112B rotate around the axis 116 relative to the first stanchion 104A and the second stanchion 104B. As such, the CT scanner 100 is movable between an upright configuration, a tilted configuration, and a horizontal configured. In some embodiments, motors (e.g., motors structured to rotate the gantry 108 relative to the stanchions 104A, 104B), electrical supply wires, and/or communications cables are provided within one or both gantry arms 112A and/or 112B.

Figure 2:
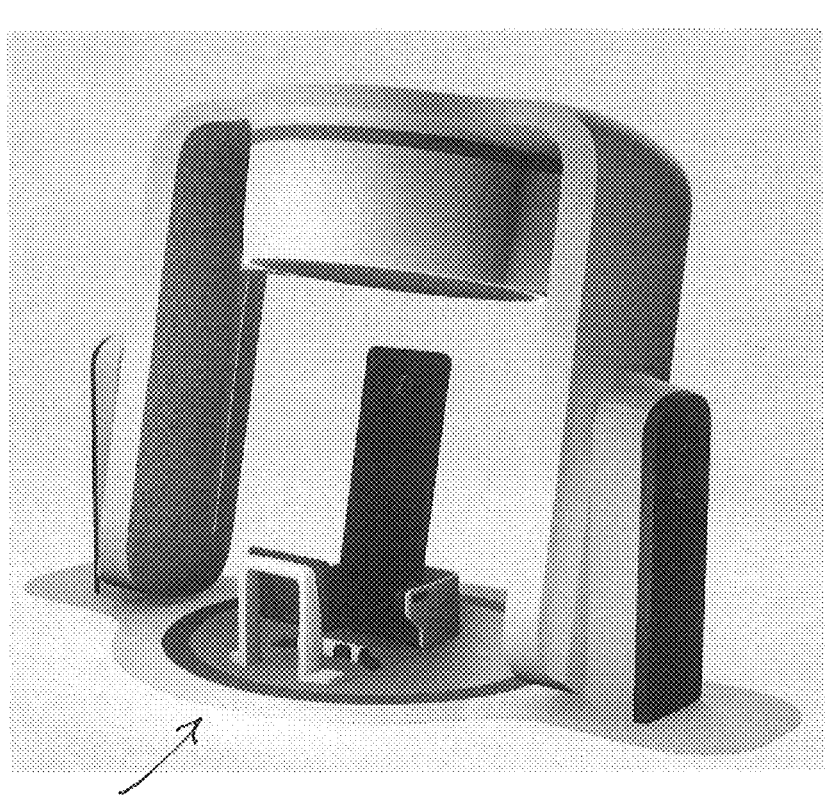
FIG. 2 is a perspective view of the scanner of FIG. 1 including a patient positioning assembly.

In some embodiments, e.g., as shown in FIG. 2, the technology provides a multi-axis CT scanner. In some embodiments, the multi-axis CT scanner is used by a user to obtain a CT scan of a patient. In some embodiments, the patient is positioned vertically. In some embodiments, a patient that is positioned vertically is positioned with a slight recline (e.g., within 20 degrees of vertical (e.g., within 5, 6, 7, 8, 9, 10, 11, 12, 13, 14, 15, 16, 17, 18, 19, or 20 degrees)) so that the patient may lean against a surface for support to provide increased immobilization of the patient and to limit motion of the patient. In some embodiments, the patient is positioned using a patient positioning system 120 and the user operates a control unit. In some embodiments, the patient positioning system 120 is as described in Int'l Pat. App. Pub. No. WO 2019/056055 and U.S. Pat. App. Pub. No. 2020/0268327, each of which is incorporated herein by reference.

Figure 3:
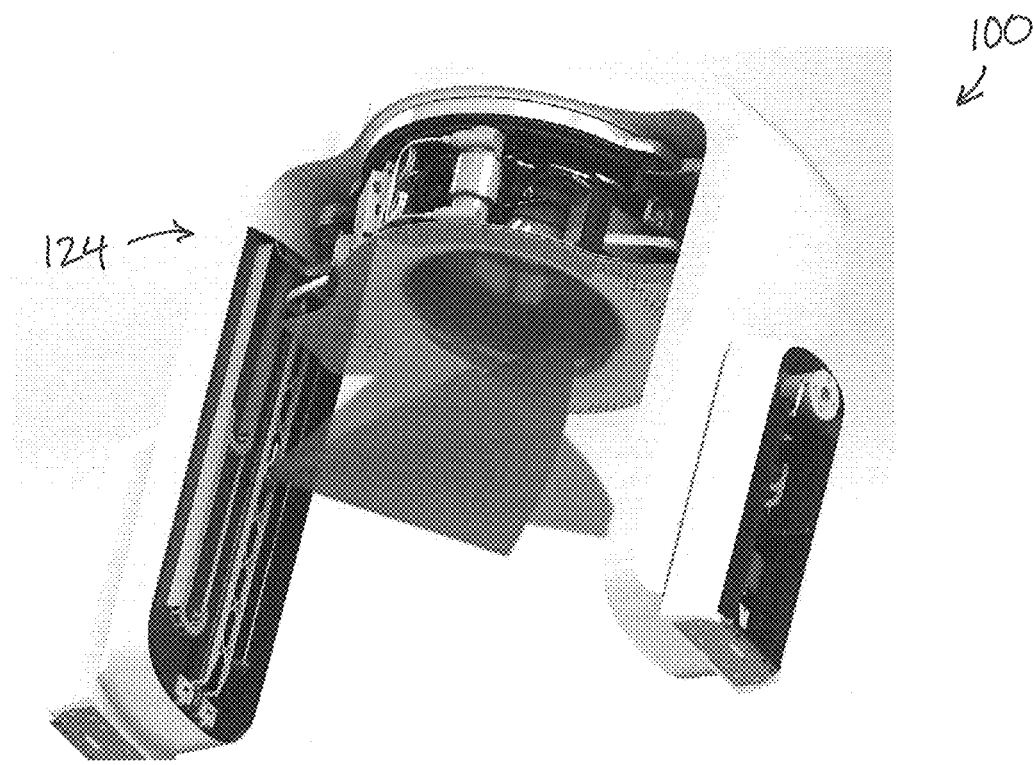
FIG. 3 is a bottom perspective tear-away view of the scanner of FIG. 1.
Figure 4:
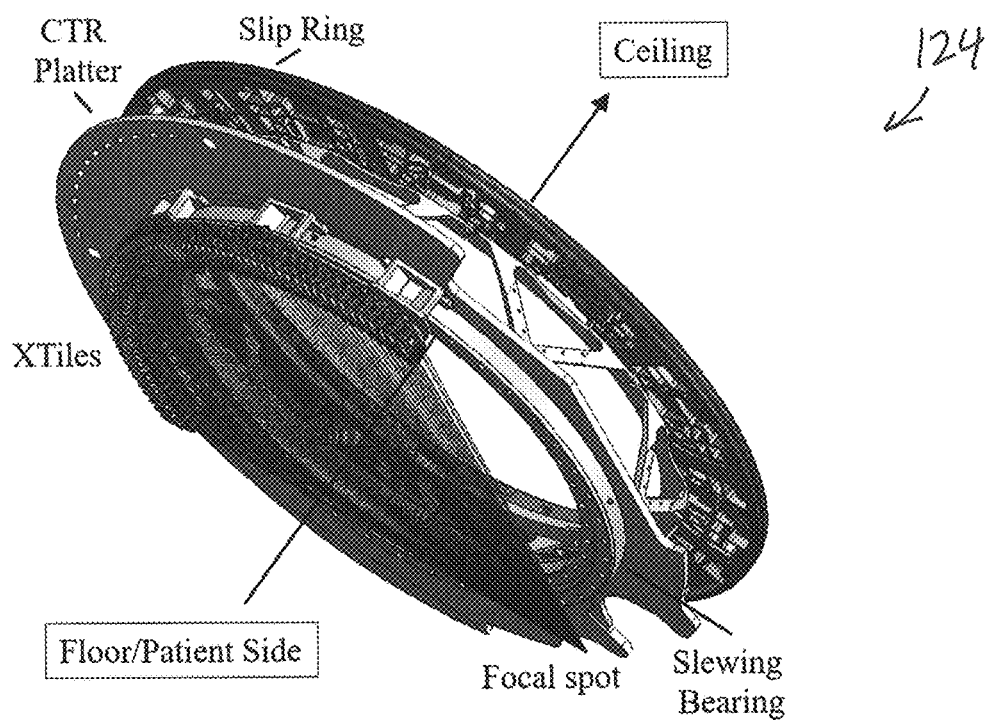
FIG. 4 is a perspective view of a scanner ring assembly of the scanner of FIG. 1.

Further, in some embodiments, as shown in FIGS. 3 and 4, the multi-axis CT scanner comprises a scanner ring 124 (e.g., a toroidal housing that comprises (e.g., encloses) a X-ray source and at least one X-ray detector). In some embodiments, rotating the gantry 108 causes the scanner ring 124 to revolve on an arc around axis 116, e.g., to move it from a first position to a second position. In some embodiments, the first position of the scanner ring 124 allows a patient to access and/or to exit the patient positioning system 120. In some embodiments, the second position of the scanner ring 124 is a position used to obtain a CT scan of a patient. In some embodiments, the second position of the scanner ring 124 is over the head of the patient.

In some embodiments, the scanner ring 124 comprises a source and a detector for CT, MRI, PET, SPECT, photon counting computed tomography, or portal imaging. Accordingly, in some embodiments, the scanner ring comprises a medical imaging source (e.g., electromagnetic radiation source, X-ray source, gamma ray source, radio wave source, photon source, proton source, positron source, gamma ray source (e.g., gamma rays from a positron source)) and a medical imaging detector (e.g., electromagnetic radiation detector, X-ray detector, photon detector, gamma ray detector), e.g., for one or more of these imaging modes.

Further, in some embodiments, the scanner ring 124 is structured to translate along an axis substantially parallel to the first gantry arm 102A and the second gantry arm 102B, e.g., along axis 128 as shown in FIG. 1. In some embodiments, the scanner ring translates along a vertical (e.g., substantially and/or essentially vertical) axis, e.g., to obtain a CT scan of a patient in a vertical position. In some embodiments, the scanner ring translates along a horizontal (e.g., substantially and/or essentially horizontal) axis, e.g., to obtain a CT scan of a patient in a horizontal position.

In some embodiments, the scanner ring 124 comprises (e.g., encloses) an X-ray generator that moves within the scanner ring 124 and thus revolves around the patient. In some embodiments, the scanner ring 124 comprises (e.g., encloses) one or more X-ray detectors. In some embodiments, the X-ray generator produces a fan beam of X-rays in a plane extending across the scanner ring.

In some embodiments, the X-ray detector comprises an arcuate detector array within said plane. In some embodiments, multiple stationary X-ray detectors are positioned around the circumference of the scanner ring 124 such that an X-ray detector is always on the opposite side of the from the X-ray source moving within the scanner ring 124. In some embodiments, the scanner ring 124 comprises a moving X-ray detector that moves within the scanner ring 124 and is positioned opposite the moving X-ray generator, e.g., the X-ray generator and the X-ray detector move in concert so that the X-ray generator and the X-ray detector are on opposite sides of the scanner ring 124. In some embodiments, the scanner ring 124 is translated into position and is stationary while the X-ray generator and X-ray detector move around the circumference of the scanner ring 124. In some embodiments, the scanner ring 124 is translated one or more times and/or is translated continuously while the X-ray generator and the X-ray detector move around the circumference of the scanner ring 124 (e.g., to provide a helical scan). In some embodiments, the multi-axis CT scanner comprises a slip ring (FIG. 4) to transmit electrical power from the scanner ring 124 to the X-ray generator and X-ray detector and to carry communications signals between the scanner ring 124 and the X-ray generator and X-ray detector.

Figure 7:
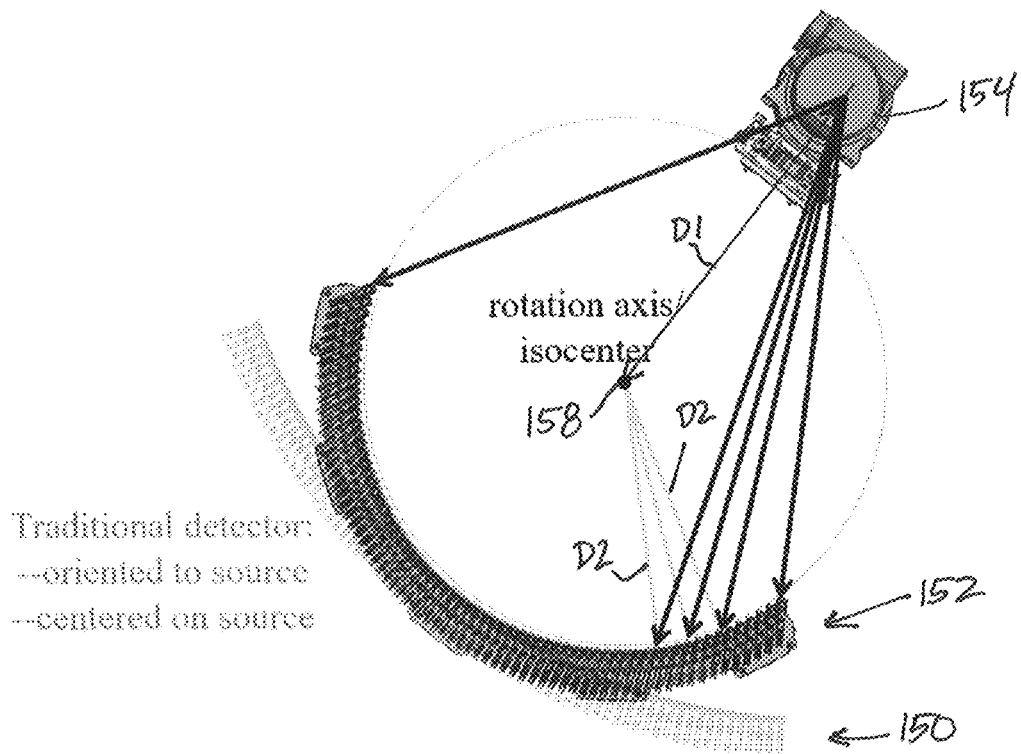
FIG. 7 is a top view of a source assembly oriented with respect to a conventional fanbeam detector assembly and with respect to a detector assembly according to embodiment disclosed herein.

In a conventional fan beam ("fanbeam") CT, the X-rays used to acquire the projections are collimated to a thin fan beam lying within the plane of the cross-section and received by a narrow linear detector. A plurality of detectors in a conventional fanbeam arrangement 150, for example illustrated in FIG. 7, are oriented to a X-ray source 154 and are centered on the X-ray source 154. In other words, in the conventional fan beam arrangement 150 each of the detectors is positioned the same, or substantially similar, distance away from the X-ray source 154. In a conventional parallel CT arrangement, the X-ray source is a series of parallel rays and the plurality of detectors are positioned the same, or substantially similar, distance away from the X-ray source.

Figure 5:
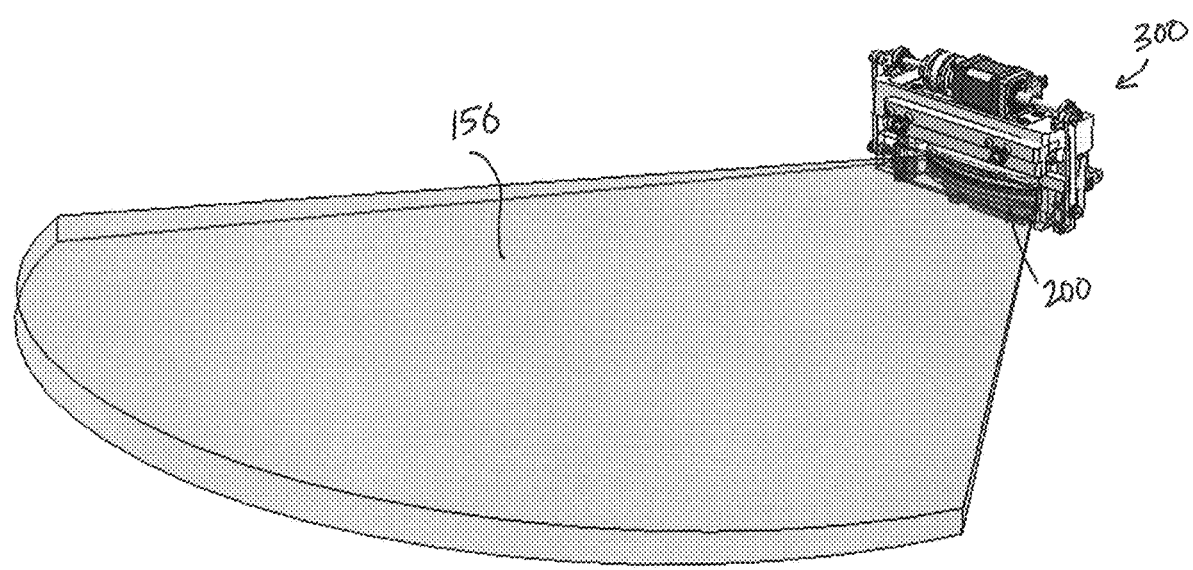
FIG. 5 is a perspective view of a source collimator assembly of the scanner of FIG. 1.

With reference to FIG. 7, the CT scanner 100 includes an isofan arrangement 152 ("isofan detector-source arrangement") positioned within the scanner ring 124. The X-ray source 154 provides a thin fan beam lying within a plane 156 (FIG. 5). The X-ray source 154 is positioned a first distance D1 from a center 158. In some embodiments, the source 154 is rotatable about the center 158. The isofan detector arrangement 152 further includes a plurality of detectors oriented to the source 154 and rotatable about the center 158. In the illustrated embodiment, the plurality of detectors 152 are positioned at varying distances from the source 154. In other words, the plurality of detectors 152 are not positioned a constant distance away from the source. In the illustrated embodiment, each of the plurality of detectors 152 is positioned a second distance D2 from the center 158. In other words, the second distance D2 (detector-to-center distance) is the same, or substantially the same. In the illustrated embodiment, the first distance D1 (source-to-center distance) is larger than the second distance D2 (detector-to-center distance).

Figure 8:
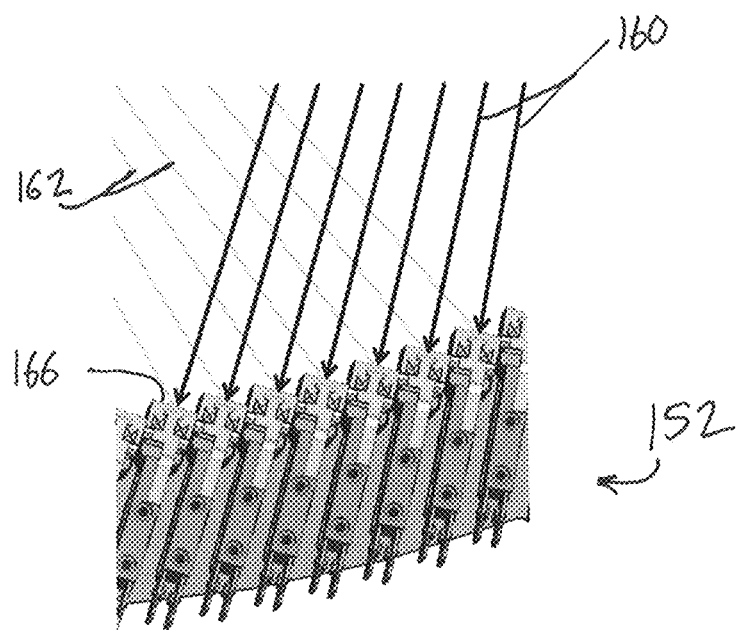
FIG. 8 is an enlarged view of the detector assembly, illustrating each of the detectors positioned the same distance from a rotational axis and oriented to the source.

With reference to FIG. 8, each of the plurality of detectors 152 is oriented to the source (see source arrows 160) and centered to a rotational axis (gray radial lines 162). In other words, the flat face of each detector module is oriented toward the source, but the modules lie on the same radius from the rotational center. Each of the plurality of detectors 152 includes a detector face 166 defining an input plane. In the illustrated embodiment, the input plane is orthogonal to the incident beam 160 from the source.

Figure 9:
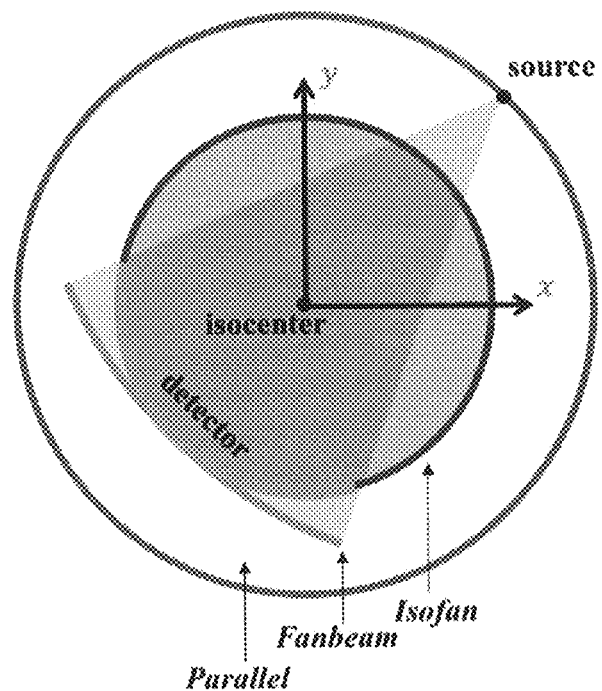
FIG. 9 is a schematic of geometric frames of reference for various source-detector systems.

With reference to FIG. 9, a comparison of the isofan arrangement to the conventional fanbeam arrangement and the conventional parallel arrangement is illustrated. In other words, FIG. 9 illustrates three geometric systems for X-ray sampling in a source-detector system. Detector samples that are physically acquired in the isofan arrangement can be transformed (rebinned) to other geometries as explained further herein.

Figure 7B:
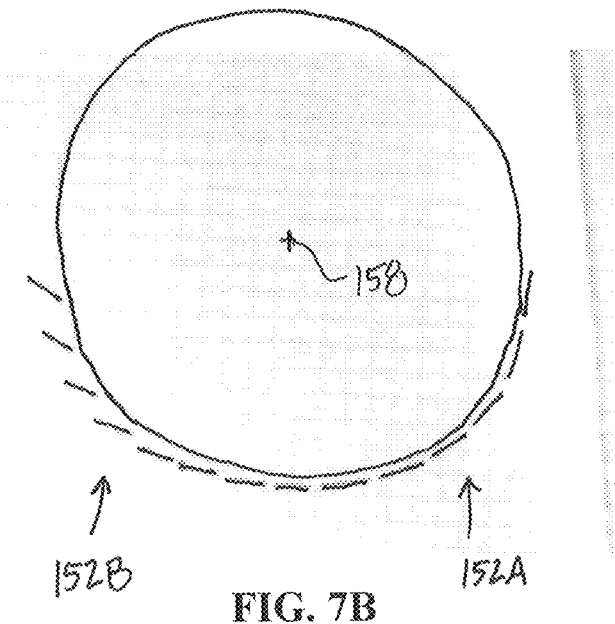
FIG. 7B is a schematic of various orientations for the plurality of detectors.
Figure 10:
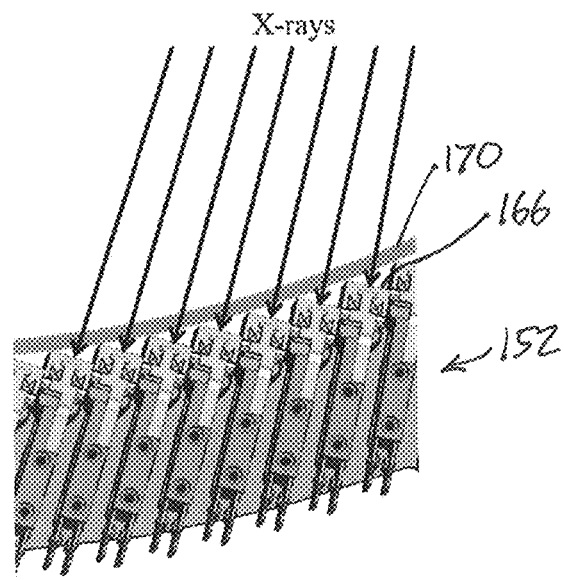
FIG. 10 is an enlarged view of the detector assembly, illustrating X-rays from a source incident on a plurality of detectors relative to a fixed radius arc, where the arc is not centered on the x-ray source.

With reference to FIG. 10, a small correction step is made to resample each flat detector module to the detector arc 170 with an equal radius from the rotational center. In other words, there is a small distance between the constant radius arc 170 and the detector surface 166 to correct for. With reference to FIG. 7B, in some embodiments, detectors 152A are oriented to the center 158 and/or some detectors 152B are oriented to the source 154. In some embodiments, each of the plurality of the detectors 152 is oriented with an edge aligned with an edge of an adjacent detector.

Figure 11:
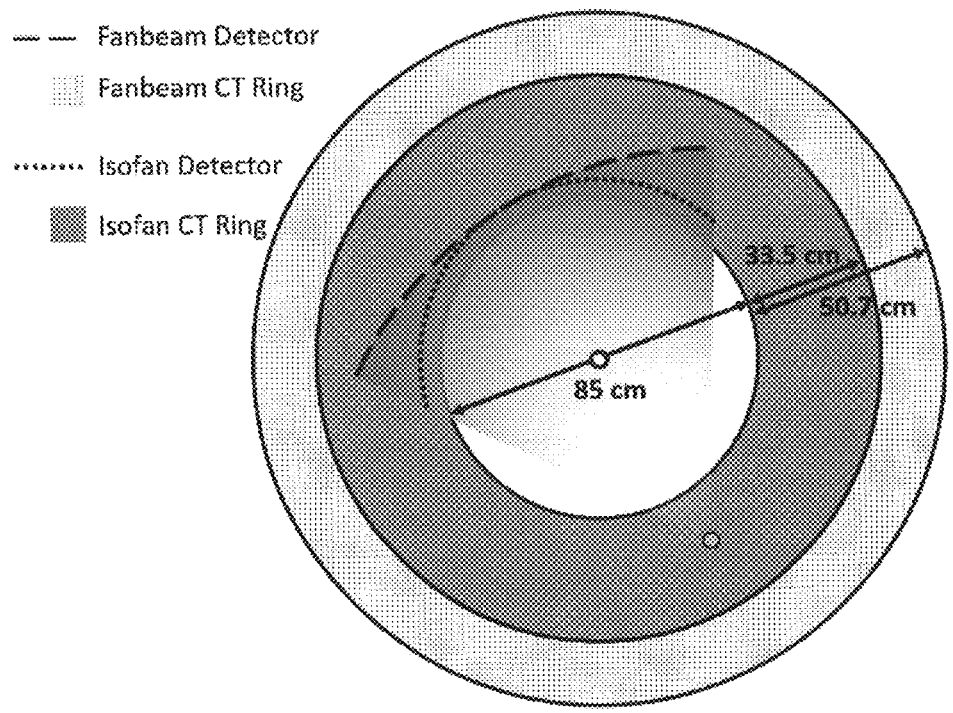
FIG. 11 is comparison of a scanner ring annulus size for a conventional detector assembly and a detector assembly as disclosed herein.

With reference to FIG. 11, the isofan arrangement allows for a tighter and smaller design of the CT scanner ring when compared to a conventional fanbeam arrangement. In the illustrated embodiment, the CT scanner ring includes a bore with an inner diameter of approximately 85 cm. With the isofan arrangement the plurality of detectors ("isofan detectors") fit within a CT ring with a thickness of approximately 33.5 cm. Compared to an equivalent fanbeam arrangement, the CT ring is approximately 50.7 cm to fit the plurality of detectors ("fanbeam detectors") collimating the same X-ray beam width. In other words, the isofan arrangement offers an approximately 34% reduction in the size of the CT ring compared to the conventional fanbeam arrangement. FIG. 11 illustrates the difference in thickness of the CT ring annulus for a conventional fanbeam arrangement and the isofan arrangement, with both having an 85 cm bore.

Figure 13:
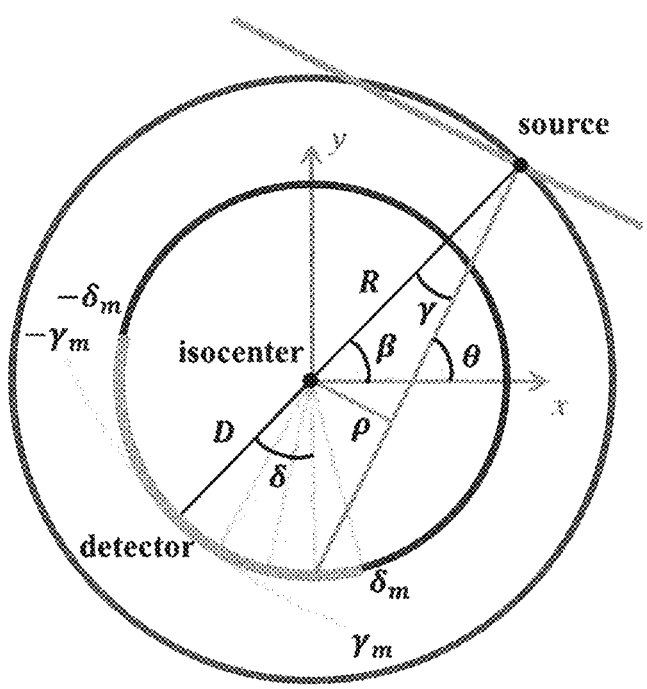
FIG. 13 is a schematic of various detector assembly geometries and related variables.

With reference to FIG. 13, various data acquisition and image reconstruction variables in the three geometric system (FIG. 9) as used herein are illustrated. Additional details for the variables illustrated in FIG. 13 are listed in Table 1.

TABLE 1

| Variable | Unit | Description |
| --- | --- | --- |
| R | mm | Source to isocenter distance |
| D | mm | Detector to isocenter distance |
| θ | radian | Source rotation angle (parallel arrangement) |
| β | radian | Source rotation angle (fanbeam and isofan arrangement) |

TABLE 1-continued

| Variable | Unit | Description |
| --- | --- | --- |
| ρ | mm | Ray sample distance (parallel) |
| Γ | radian | Ray sample angle (fanbeam arrangement) |
| Δ | radian | Ray sample angle (isofan arrangement) |
| $Y_m$ | radian | Maximum fanbeam angle |
| $\delta_m$ | radian | Maximum isofan angle |
| t | s | Time (t = 0 is defined at β = θ = 0) |

For simplicity in the derivations and explanations that follow, a constant velocity for the tube rotation is assumed. Therefore, the source rotation angle is directly proportional to time, that is β∝t and θ∝t. However, in other embodiments, the scanner is operated with a variable tube rotation velocity.

Figure 12:
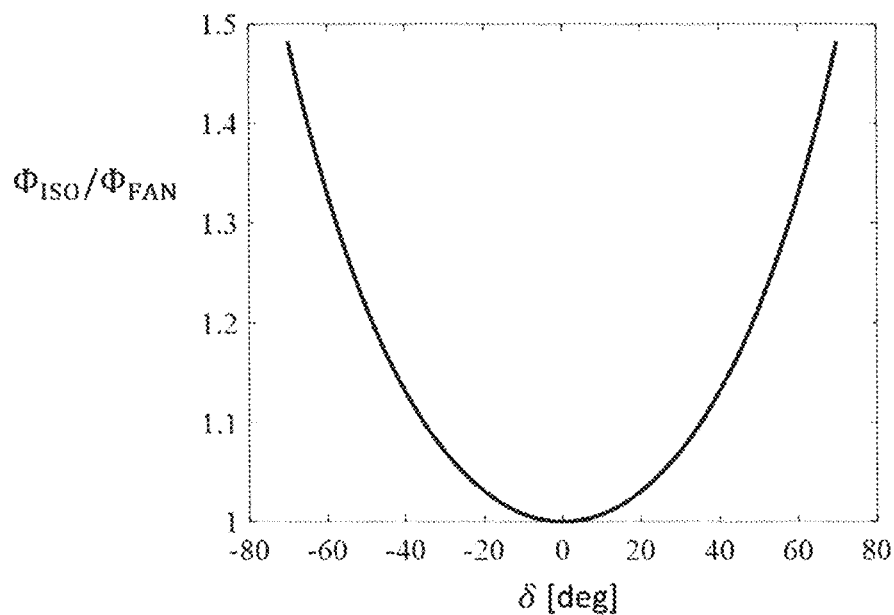
FIG. 12 is a graph of a ratio of the X-ray flux at the detector assembly disclosed herein to the X-ray flux at a conventional fanbeam detector assembly for a given detector position, δ.

With reference to FIG. 12, the isofan detector arrangement also has the benefit of increasing the flux at the detectors. Geometric attenuation of X-ray follows an inverse square relationship (flux, $\Phi \propto 1/r^2$). As such, by bringing the detectors closer to the source than those in a conventional fanbeam geometry, the flux attenuation is less (i.e., a higher flux reaches the isofan detectors). The relationship between the flux reaching the isofan detectors ($\Phi_{iso}$) and the flux reaching the conventional fanbeam detectors ($\Phi_{fan}$) is provided by the ratio of EQN. 1.

$$\frac{\Phi_{ISO}}{\Phi_{FAN}} = \frac{(R+D)^2}{R^2 + D^2 + 2RD \cos \delta} \qquad \text{EQN. 1}$$

This ratio is plotted in FIG. 12 for values of R and D and the range of −70°≤δ≤70° corresponding to one embodiment. In some embodiments, the variance of photon fluence among the plurality of detectors is less than 50%.

Figure 14:
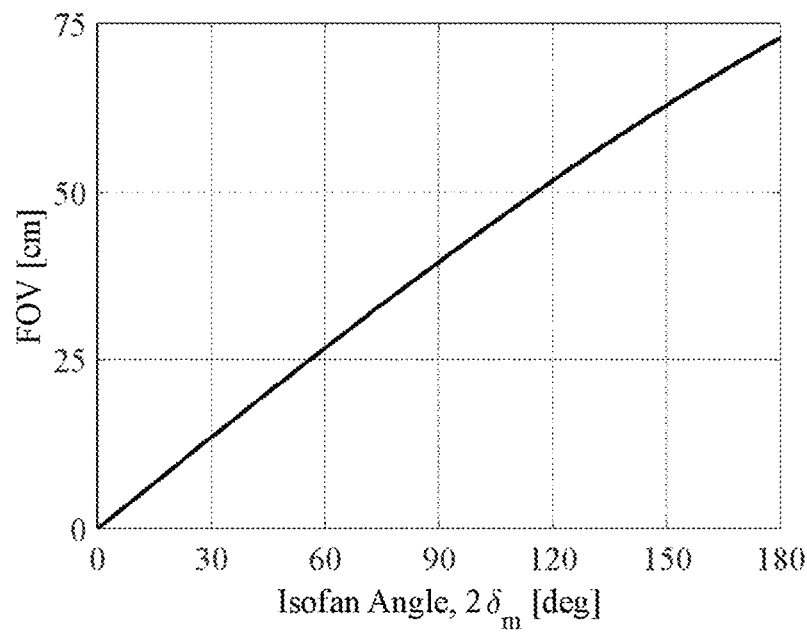
FIG. 14 is a graph of the scanner field of view as a function of the detector assembly angle.

With reference to FIG. 14, the scan field of view (FOV, a.k.a. field of vision) for the isofan detector arrangement is illustrated as a function of the full width of the isofan angle $2\delta_m$. In some embodiments, the field of view is approximately 75 cm. in some embodiments, the plurality of detectors define a field of view of at least approximately 50 cm.

Figure 6A:
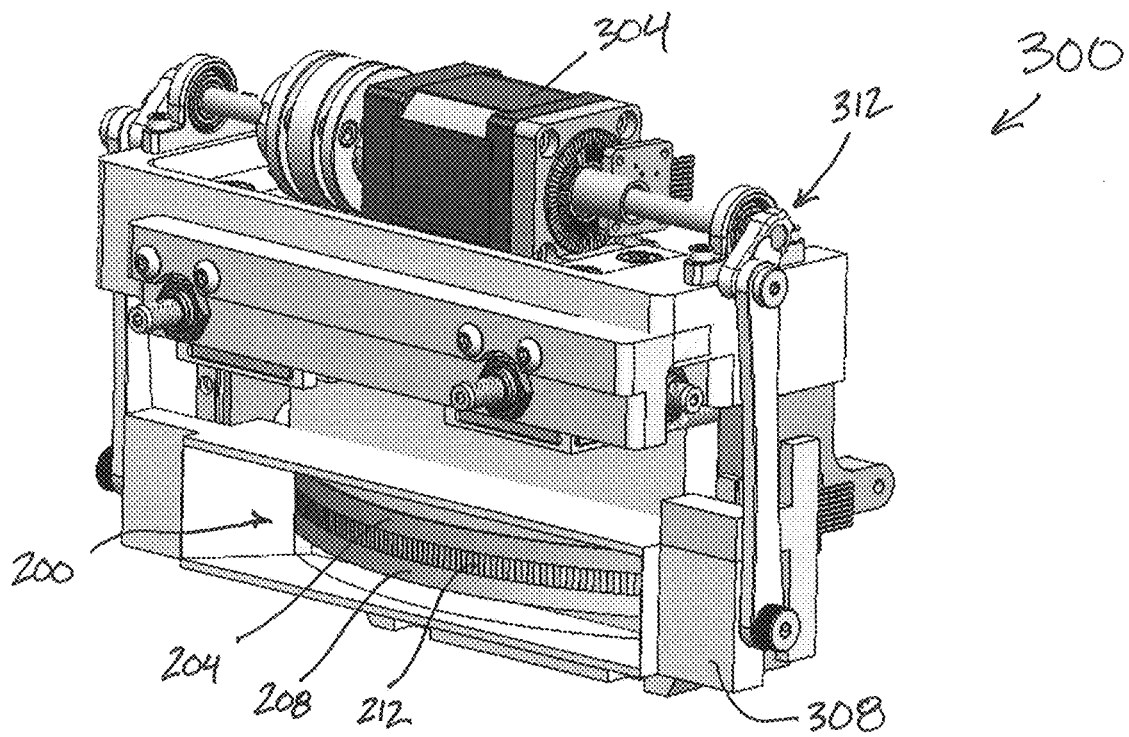
FIG. 6A is a perspective view of the source collimator assembly of FIG. 5, shown with a filter in a first position (e.g., bottom position).
Figure 6B:
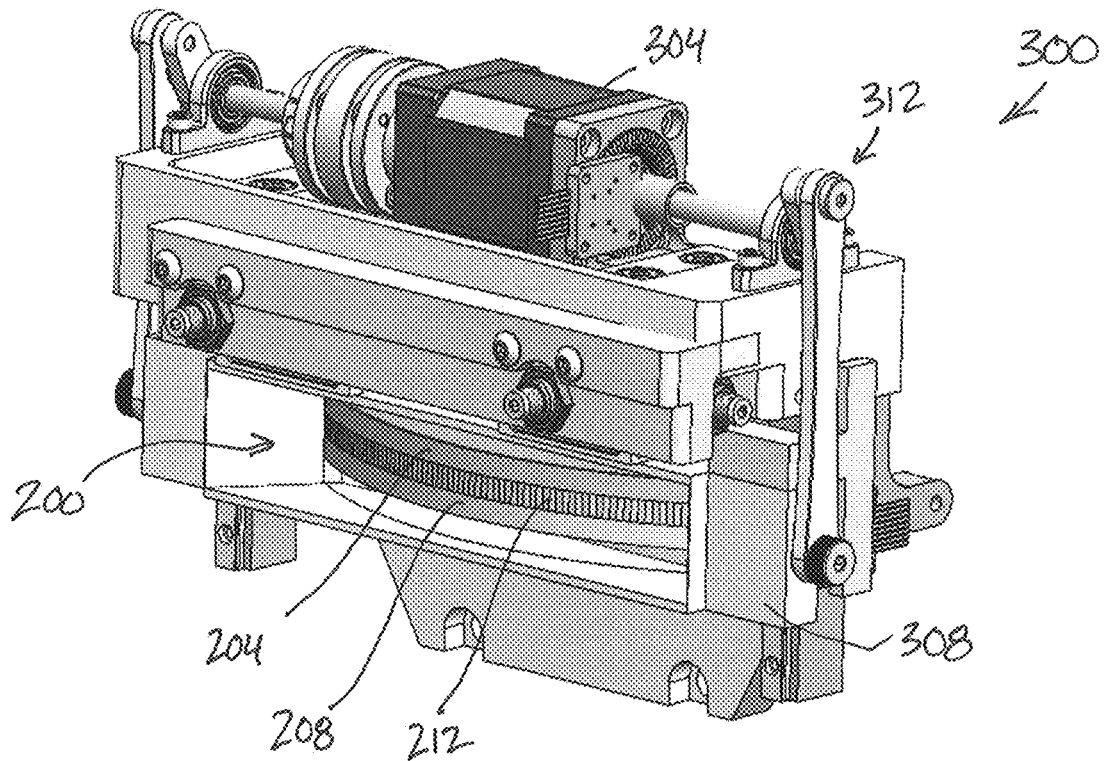
FIG. 6B is a perspective view of the source collimator assembly of FIG. 5, shown with the filter in a second position (e.g., top position).

With reference to FIGS. 6A, 6B, and 18, the CT scanner 100 includes a filter 200. The filter 200 is positioned at or near the X-ray source 154. In other words, the filter 200 is positioned closer to the source 154 than to any one of the detectors 152. As described elsewhere herein, the source 154 emits a spectrum in an imaging plane 156 (FIG. 5).

In the illustrated embodiment, the filter 200 is a dual-energy filter. The filter 200 includes a first filter portion 204 including a first material, a second filter portion 208 including a second material, and a third filter portion 212 including the first material and the second material. In the illustrated embodiment, the third filter portion 212 is positioned between the first filter portion 204 and the second filter portion 208 and includes alternating columns of the first material and the second material (alternating windows of the first and second materials) that intersect the imaging plane 156. In some embodiments, the first filter portion at least partially overlaps with the third filter portion and the second filter portion at least partially overlaps with the third filter portion (there is an overlapped transition between the filter portions). In the illustrated embodiment, the filter 200 is arcuate and defines a fixed radius. In other embodiments, the filter defines a variable radius. In other embodiments, the filter planar and not curved. In some embodiment, the filter includes five or more distinct portions of different materials. In some embodiments, the filter includes an air portion. In other embodiments, the filter includes an aluminum filter or bowtie profile portion.

In some embodiments, the first material attenuates an X-ray spectrum a first amount and the second material attenuates the X-ray spectrum a second amount, different than the first amount. For example, the first material can provide a low energy spectrum and the second material can provide a high energy spectrum. In other words, the two materials have different mass attenuation coefficients (that are dependent on both density and atomic number) so that different outgoing photon spectrum with separated mean energies are used to inspect the object with. For example, an original spectrum of 140 kVp photons (energies 0-140 keV) passing through the first material or the second material will yield different outgoing spectra. A first order measure of each spectra is the mean photon energy of each. Therefore, the first material will yield a photon spectrum with a mean energy $E_a$ to probe the object and the second material will yield a photon spectrum with a mean energy $E_b$ to probe the object. It can be advantageous to have $E_a$ and $E_b$ be far apart.

In some embodiments, the first material has a first mass attenuation coefficient within a range of 0.1 cm$^2$/g to 200 cm$^2$/g (e.g., 0.1, 0.5, 1, 5, 10, 50, 100, 150, 200) corresponding to an excitation within a range of 10 to 200 kVp (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200), and the second material has a second mass attenuation coefficient different than the first mass attenuation coefficient for the excitation. In some embodiments, the first mass attenuation coefficient and the second mass attenuation coefficient for a given excitation level (e.g., 140 kVp) are separated by at least an order of magnitude. In some embodiments, the first mass attenuation coefficient and the second mass attenuation coefficient for a given excitation level are separated by at least two orders of magnitude. In some embodiments, the first mass attenuation coefficient is approximately 10 cm$^2$/g at an excitation of approximately 140 kVp and the second mass attenuation coefficient is approximately 1 cm$^2$/g at the same excitation.

In some embodiments, the first material is gold (Au). In some embodiments, the second material is molybdenum (Mo). In some embodiments, the second material is tin (Sn).

Figure 19:
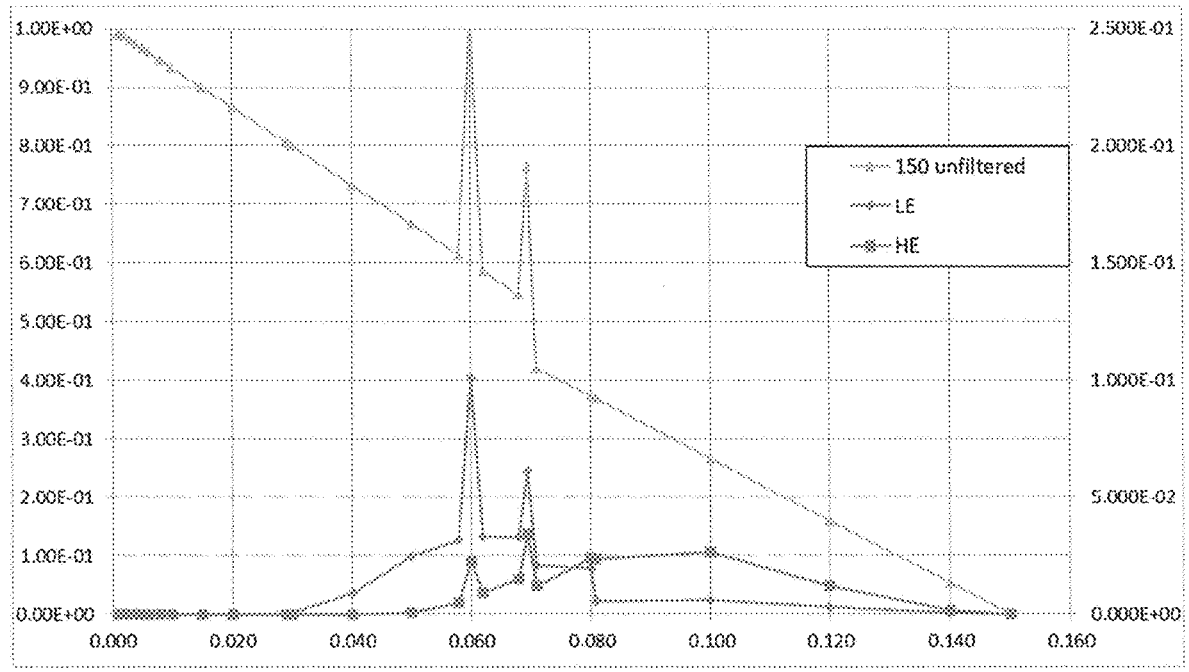
FIG. 19 is a graph illustrating X-ray energy spectra for the low energy and high energy of the dual-energy filter of FIG. 18.

With reference to FIG. 19, the X-ray spectra for the low-energy first filter portion and the high energy second filter portion are illustrated. The 150 kVp unfiltered spectrum is used to normalize each spectra, with the left vertical axis the max value and the right vertical axis the unit area. In some embodiments, the high energy range and the low energy range are separated by an energy cutoff. In some embodiments, the energy cutoff is approximately 80 kV. In other embodiments, the energy cutoff is within a range of approximately 60 kV and approximately 100 kV.

With reference to FIGS. 6A and 6B, the CT scanner includes a filter adjustment assembly 300 positioned within the CT scanner ring. The filter adjustment assembly 300 includes a motor 304, a frame 308, and a linkage 312 coupled between the motor 304 and the frame 308. In the illustrated embodiment, the dual energy filter 200 is coupled to the frame 308. As such, the filter 200 is movable with respect to the X-ray source to align any one of the first filter portion 204, the second filter portion 208, and the third filter portion 212 with the imaging plane. In other words, the filter adjustment assembly 300 translates the filter 200 with respect to the source in order to align the desired filter portion with the X-ray beams. FIG. 6A illustrates the filter 200 in a first position (e.g., bottom position), and FIG. 6B is illustrates the filter 200 in a second position (e.g., top position).

Single Energy Scan Reconstruction

For acquisitions at a single energy, CT image reconstruction for the CT scanner is provided by taking the native acquisition data in the isofan arrangement (isofan geometry) and applying a direct analytical reconstruction of the isofan rays. This entails making a transformation of variables from equations for parallel beam (Kak) or fanbeam filtered back projection (Feldkamp) reconstruction, and performing similar steps to those reconstructions (e.g. weighting the data for geometric corrections, filtering, and backprojecting) except where the exact parameters in those steps are determined by the transformation of variables. Kak, A. C., Principles of Computerized Tomographic Imaging, 2001; Feldkamp, L. A., Practical Cone-Beam Algorithm, Journal of the Optical Society of America, 1984; 1:612-619.

Alternatively, the CT image reconstruction is provided by taking the native acquisition data in the isofan geometry and rebinning (transforming) the isofan data to the fanbeam geometric frame of reference. Rebinning isofan sampled data to fanbeam geometry is provided by EQN. 2:

$$\tan \gamma = \frac{D \sin \delta}{R + D \cos \delta} \quad \text{EQN 2}$$

With the rebinned fanbeam data, a conventional fanbeam reconstruction algorithm can be utilized. Alternatively, the fanbeam data can again be rebinned as parallel beam geometry and conventional parallel beam reconstruction algorithms can be used. Rebinning fanbeam data to parallel beam geometry is provided by EQN. 3:

$$\theta = \beta + \gamma$$

$$\rho = R \sin \gamma \quad \text{EQN 3:}$$

Notably, using a conventional fanbeam or parallel beam reconstruction algorithm for the sampled data with isofan geometry does not have a significant impact on reconstruction accuracy. This is because the rebinning from isofan to fanbeam is very close to a linear conversion throughout the reconstruction field-of-view (FOV). The first order approximation to EQN. 2 is shown as EQN. 4.

$$\gamma = \frac{D}{R + D} \delta \quad \text{EQN. 4}$$

Figure 25A:
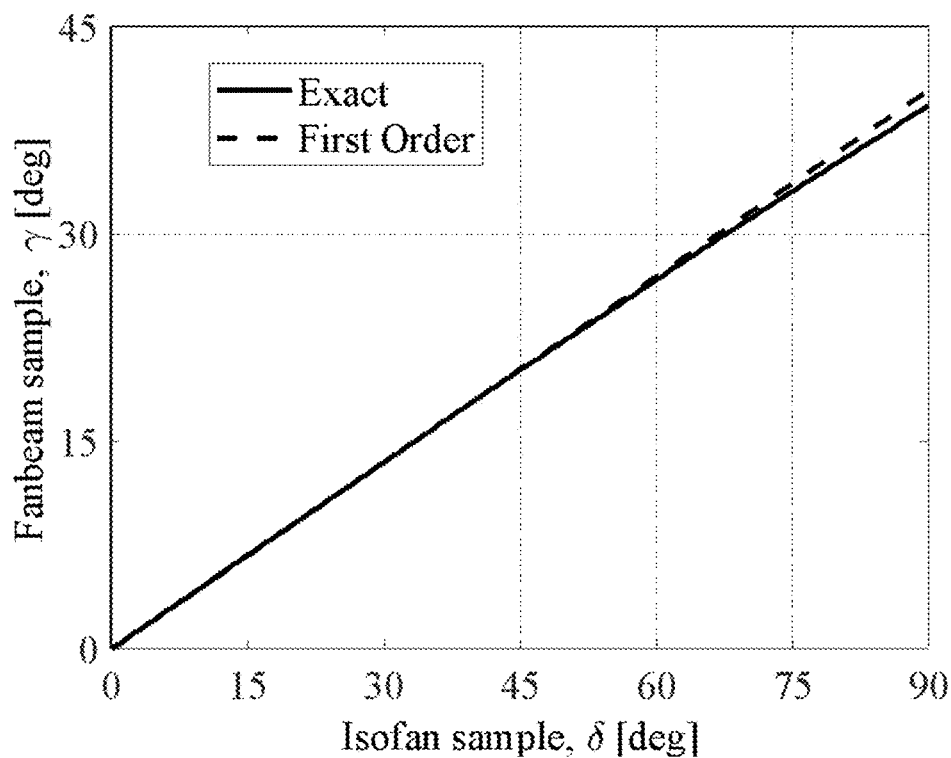
FIG. 25A is a graph comparison of a first order approximation of a fanbeam sample with respect to an isofan detector angle.
Figure 25B:
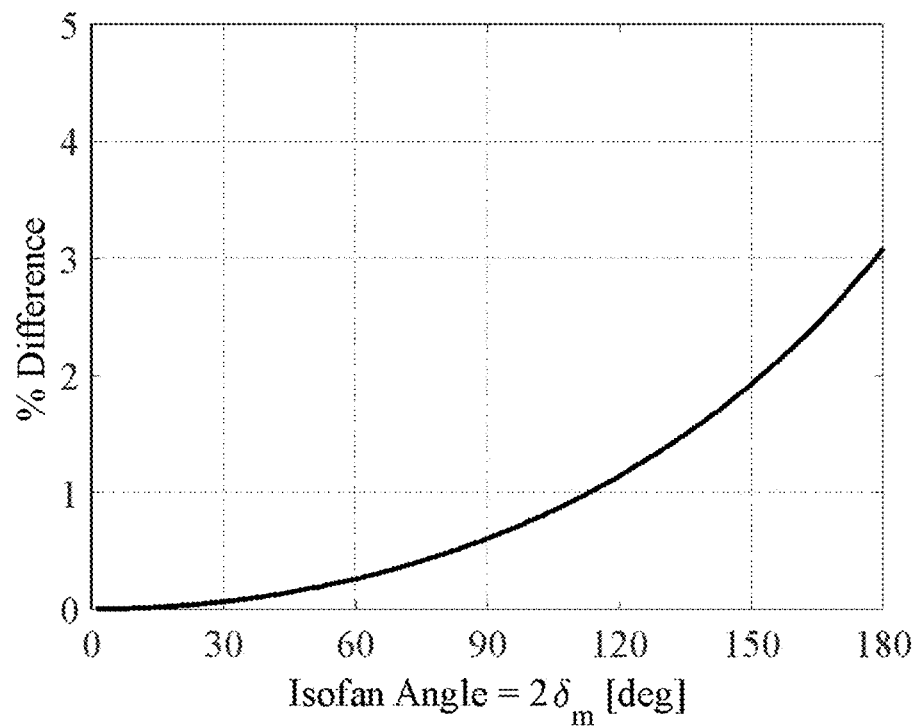
FIG. 25B is a graph of the percent error for the linear approximation of FIG. 25A as a function of the detector angle.
Figure 25C:
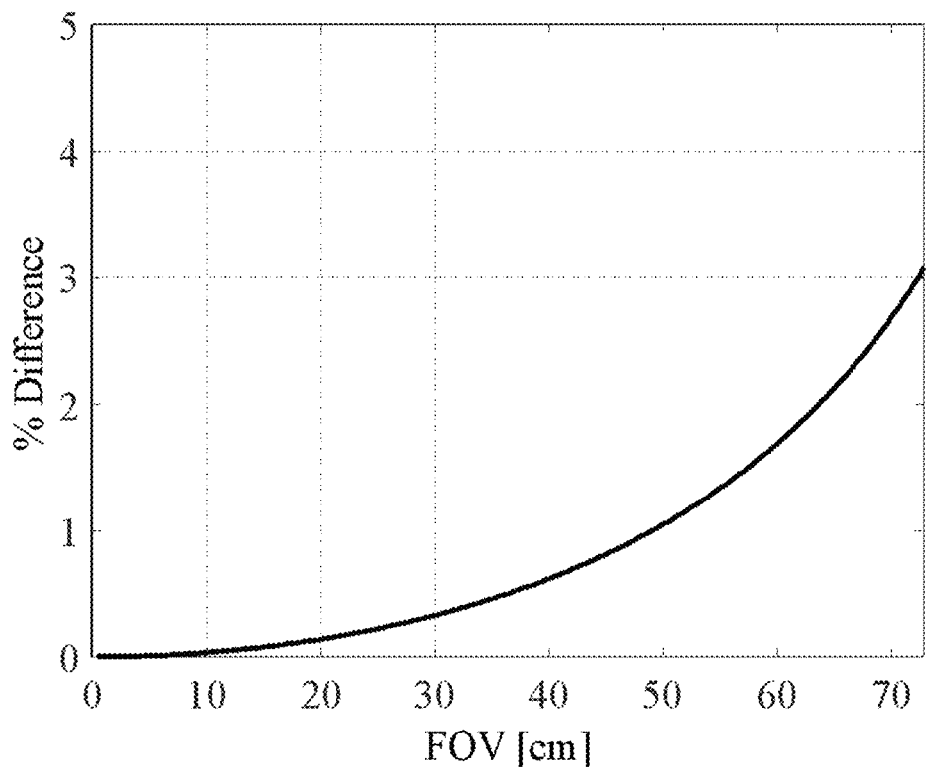
FIG. 25C is a graph of the percent error for the linear approximation of FIG. 25A as a function of the field of view.

Both EQN. 2 and EQN. 4 are plotted in FIG. 25A. The percent error (%-error) for the linear approximation (EQN. 4) plotted in FIGS. 25B, 25C as a function of the full isofan angle or equivalently reconstruction field of view, is less than 3% for the entire field of view. In other words, FIGS. 25A-25C illustrate the γ-δ relationship and its 1$^{st}$ order approximation given by EQN. 2 and EQN. 3.

Figure 26A:
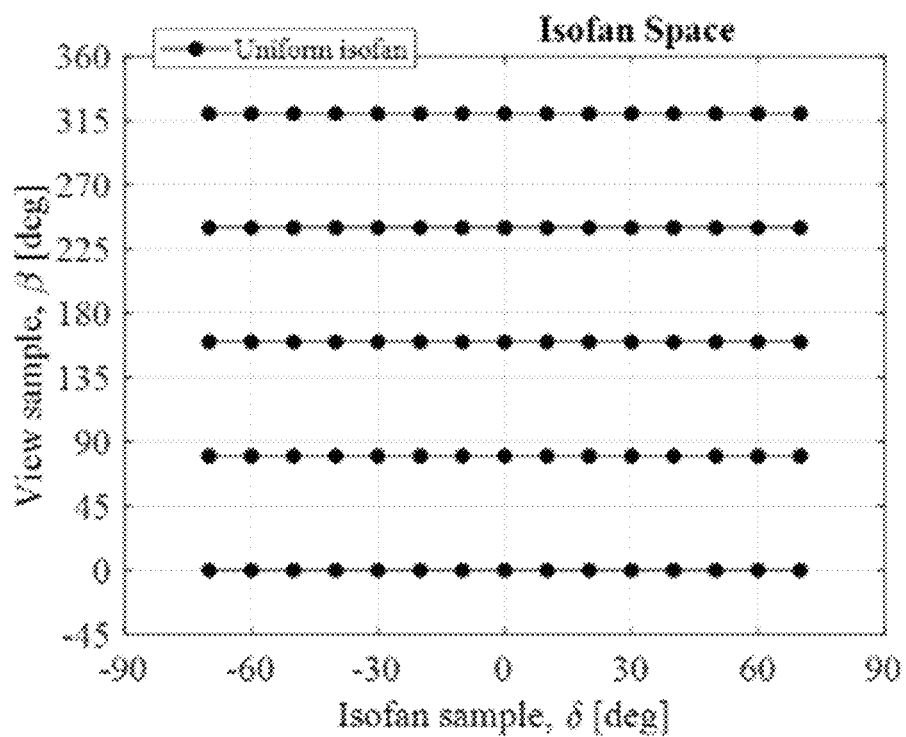
FIG. 26A is a graph of uniform isofan sampling.
Figure 26B:
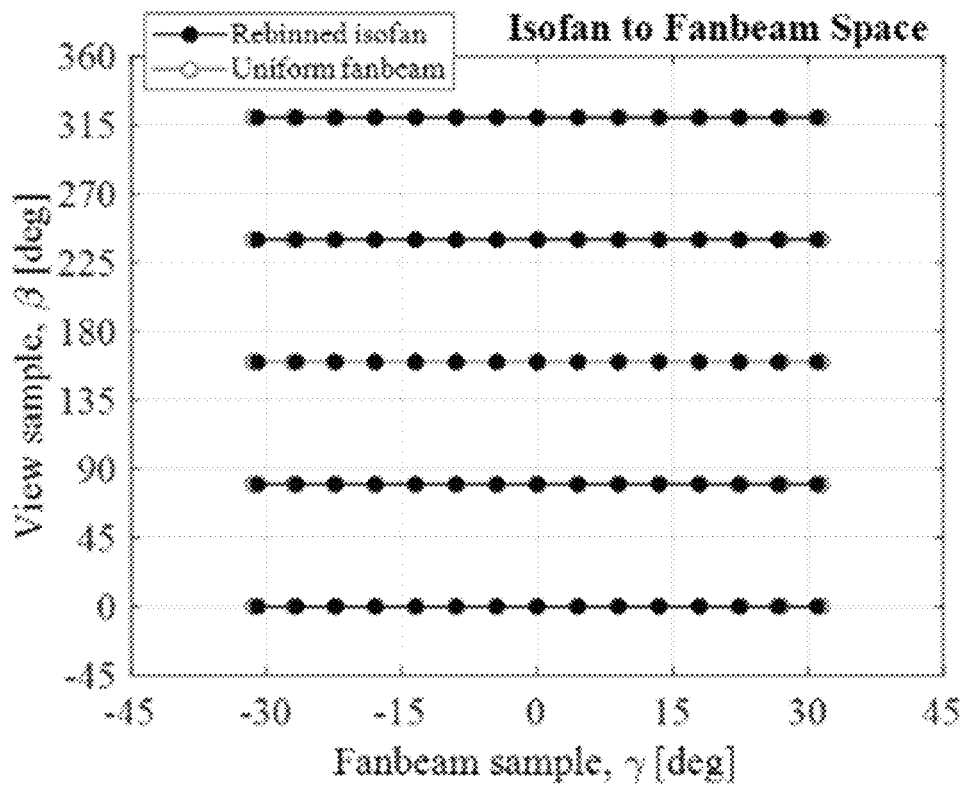
FIG. 26B is a graph of the uniform isofan sampling rebinned to a fanbeam geometry, shown overlaid with uniform fanbeam sampling for reference.
Figure 26C:
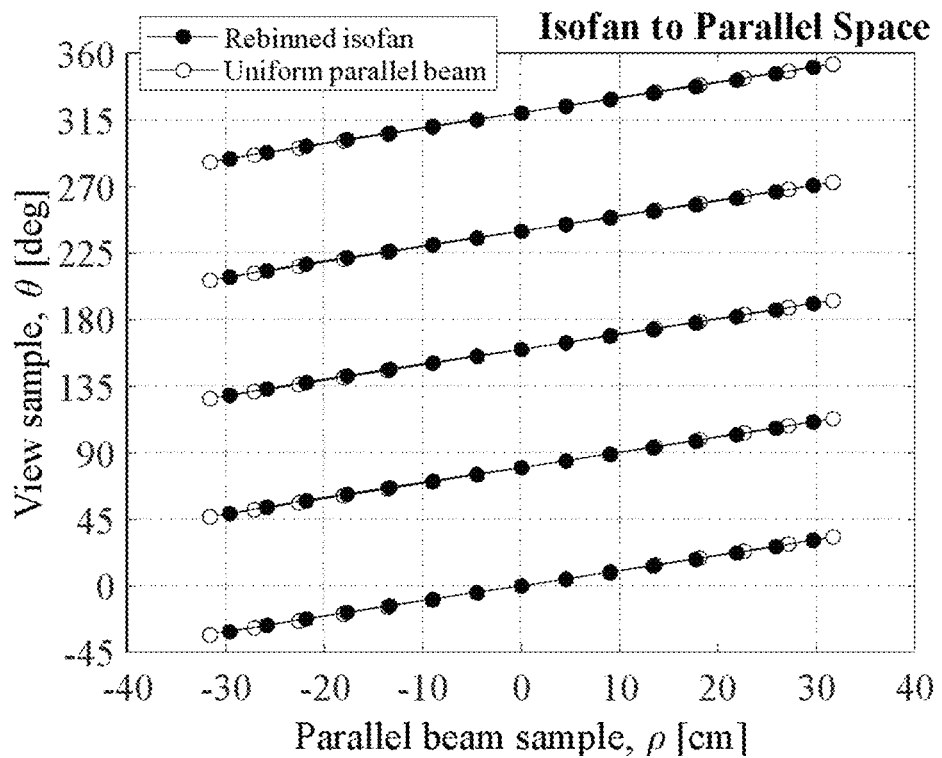
FIG. 26C is a graph of the uniform isofan sampling rebinned as a parallel beam geometry, shown overlaid with uniform parallel beam sampling for reference.

With reference to FIGS. 26A-26C, the effect of the near linear rebinning scheme is illustrated. The native isofan samples (FIG. 26A) are rebinned to fanbeam space (FIG. 26B) and parallel space (FIG. 26C) and compared to samples natively taken in the respective fanbeam and parallel space. In other words, uniform sampling in the isofan space (δ=nΔδ) (FIG. 26A) is rebinned to the auxiliary spaces in the fanbeam geometry (FIG. 26B) and the parallel beam geometry (FIG. 26C). For comparison, uniform sampling in each of the auxiliary spaces (fanbeam, $\gamma=n\Delta\gamma$) (parallel, $\rho=n\Delta\rho$) is shown with the rebinned isofan samples. As shown in FIG. 26B, the rebinned isofan samples are almost identical to fanbeam samples acquired directly.

An advantage of the isofan arrangement is that it has an improved image noise performance when compared to fanbeam acquisition geometry because of the higher photon flux reaching the detectors on the edge because they are physically positioned closer to the X-ray source in isofan than fanbeam. See, for example, FIG. 12.

Dual Energy Scan Reconstruction

To reconstruct a CT image with limited view artifacts, the Tuy data sufficiency condition for CT stipulates the minimum angular scan range required. Tuy HK. An inversion formula for cone-beam reconstruction. SIAM J Appl Math. 1983; 43: 546-52. For conventional fanbeam CT acquisition, the data sufficiency condition is $180°+2\gamma_m$, where $2\gamma_m$ is the full fan angle. For a fan angle of $2\gamma_m=60°$ (approximate angle for conventional systems), this minimum scan range is thus 240°. Therefore, a complete data set for a single image reconstruction can be acquired with a 240° scan.

Figures 15A, 15B:
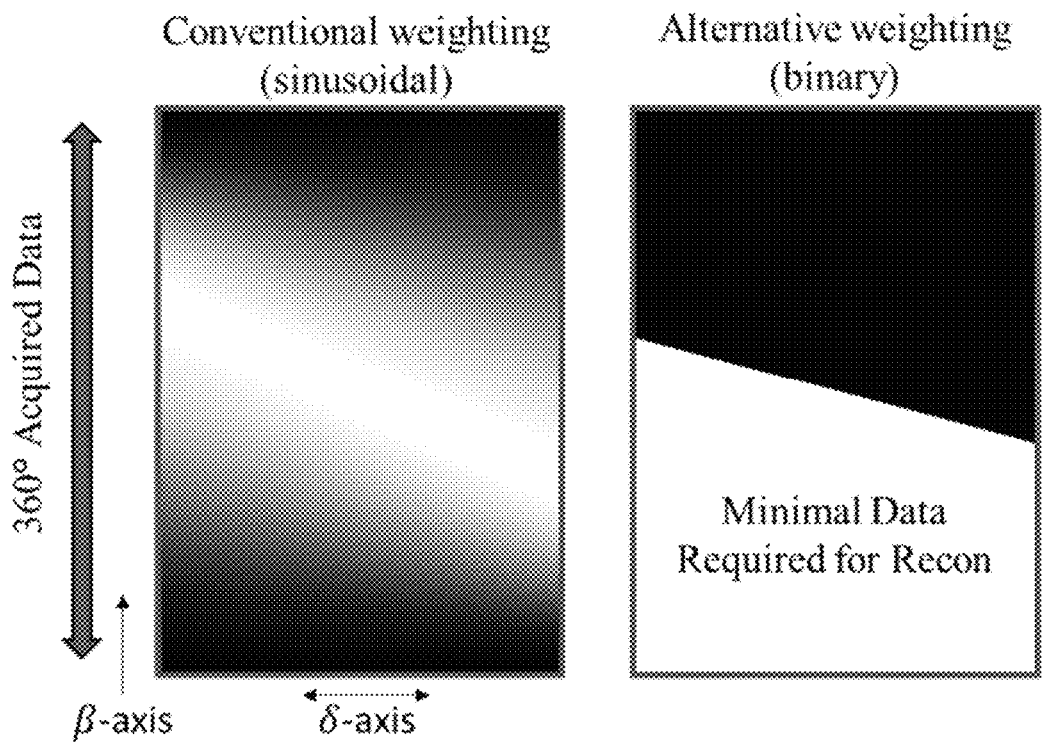
FIG. 15A-15B illustrates sinusoidal and binary weighting of data acquired by the detector assembly.

Obtaining two complete data sets, however, does not require double the minimum scan range (e.g., 480°). In other words, a 360° fanbeam acquisition contains two complete data sets that meet the 240° minimum. With reference to FIG. 15B the two trapezoidal sampling regions—one black, one white—in the 360° sinogram space illustrate the two complete data sets. Geometrically, the trapezoids are conjugate to each other, meaning each X-ray sample $s(\gamma,\beta)$ is measured exactly twice. Hence for 360° scans, there are exactly two sets of redundant data that can be used for reconstruction.

As an example, the conjugate sample $s_2=s(\gamma_2,\beta_2)$ to a sample $s_1=s(\gamma_1,\beta_1)$ in fanbeam space is given by the following EQN. 5-6:

$$\begin{cases} \gamma_2 = -\gamma_1 \\ \beta_2 = \beta_1 + \pi + 2\gamma_1 \end{cases} \qquad \text{EQNS. 5-6}$$

Note that without loss of generality, we are defining $s_2$ to be sampled later in time than $s_1$, and since $\beta \propto t$ in the constant tube velocity case, we have $\beta_2 > \beta_1$. To reconstruct an image, weights $w_1$ and $w_2$ are utilized for two X-ray samples that are conjugate to each other. The sample $s^*$ to be used for reconstruction is calculated as EQN. 7:

$$s^* = w_1 \cdot s_1 + w_2 \cdot s_2 \qquad \text{EQN. 7:}$$

Practical reconstruction theory requires the weights satisfy $w_1, w_2 \geq 0$ and $w_1+w_2=1$. For single energy CT scans with scan ranges greater than 180°+ fan angle and less than 360°, the weights $w_1$, $w_2$ are conventionally determined using various methods, including those of Parker (i.e. the sinusoidal weights shown FIG. 15A) or Crawford and King. See Parker, D L, Optimal short scan convolution reconstruction for fanbeam CT, Medical Physics, 1982; 9:254-257. See also Crawford, C R and King, K F, Computed tomography scanning with simultaneous patient translation, Med. Phys., 1990; 17:967-982.

Figure 20:
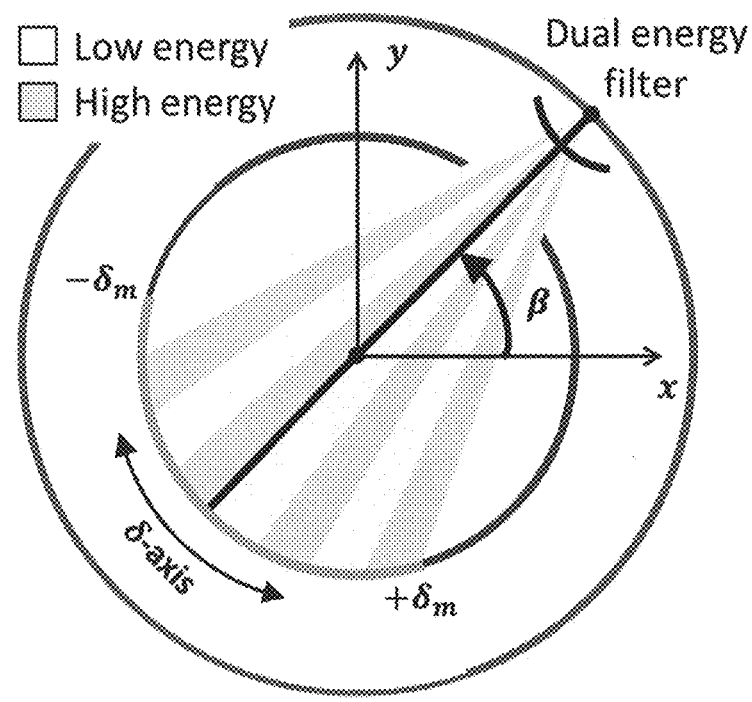
FIG. 20 is a schematic of a source and a detector assembly including a dual energy filter, illustrated with four low energy zones and four high energy zones oriented radially.
Figure 21:
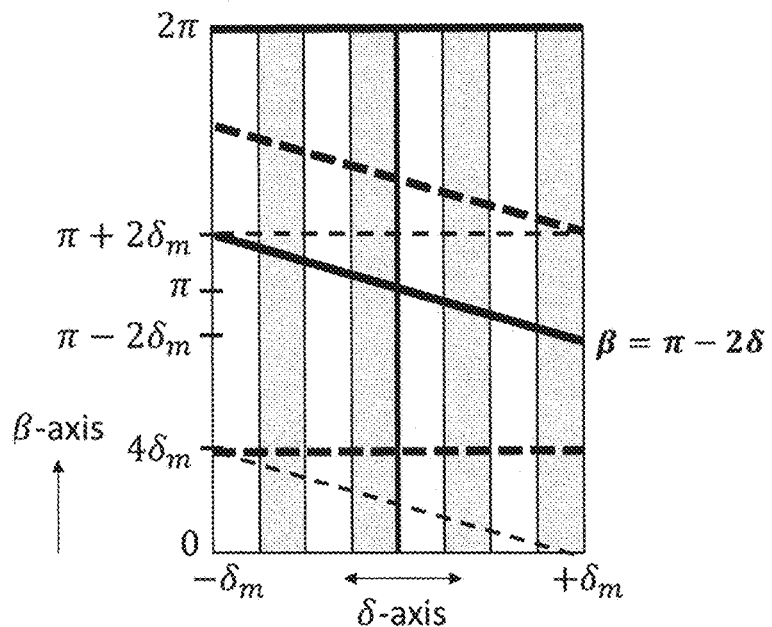
FIG. 21 is a sinogram of the acquired dual energy data for a single revolution.

For a dual energy scan using the proposed method described herein, a low energy (LE) image and a high energy (HE) image can be reconstructed by taking advantage of the conjugacy. With reference to FIG. 20-21, every X-ray sample is sampled twice with a single rotation, but because the energy regions alternate along the detector channels, each sample is taken once with the LE spectrum and once with the HE spectrum. However, proper artifact-free reconstruction requires each X-ray view is comprised of samples from the same energy spectrum. Supposing $s_1=s(\gamma_1,\beta_1)$ is a HE sample, then $s_2=s(\gamma_2,\beta_2)=s(-\gamma_1,\beta_1+\pi+2\gamma_1)$ will be a LE sample, and the LE and HE data sets at the point $(\gamma_1,\beta_1)$ in sinogram space can be formed using binary weights, EQN. 8:

$$s^{LE}(\gamma_1,\beta_1)=0 \cdot s_1+1 \cdot s_2 \qquad \text{EQN. 8:}$$

For the view at $\beta_1$ therefore, the missing low energy data is filled in with the corresponding low energy data from its conjugate view later in the scan. Similarly, missing high energy data in view $\beta_2$ is filled in with conjugate high energy data from an earlier view:

$$s^{HE}(\gamma_2,\beta_2)=1 \cdot s_1+0 \cdot s_2$$

With reference to FIGS. 16A-16D, a simplified example of conjugate X-rays in a dual energy scanning system are illustrated. In FIG. 16A, three X-ray samples A, B, and C are acquired. Sample A is acquired at high energy (dark grey region) and samples B and C are acquired at low energy (light grey region). FIGS. 16B, 16C, and 16D illustrate the conjugate ray for each of the samples. With reference to FIG. 16B, the conjugate ray to sample A is sample A', which is acquired at low energy. As such, the same object data is measured on the X-ray path corresponding to A or A', once at high energy and once at low energy. Similarly, with reference to FIGS. 16C and 16D, paths B and B' and C and C' are conjugate pairs with one sample measured at each energy level.

In some embodiments, the data completion module utilizes data conjugacy. With reference to FIGS. 17A-17C, the conjugacy can be used to complete the required data sets at each energy level for image reconstruction. In other words, FIGS. 17-17C illustrate the concept of conjugate data completion with a simplified dual energy case with only two energy windows. FIG. 17A illustrates where samples A, B, and C and their respective conjugate pairs A', B', and C' are acquired in a sinogram space. For low energy image reconstruction, conjugate data from the region containing sample A' can be used to replace the data block containing sample A. As such, FIG. 17B is formed and has one complete data set (native samples B and C and conjugate sample A') that can be used to reconstruct the low energy image. Similarly, in FIG. 17C, the conjugate block from FIG. 17A that contains samples B' and C' are used to complete the data set required for the high energy image reconstruction (native sample A and conjugate samples B' and C').

With reference to FIGS. 20-21, the simplified example of FIGS. 16A-16D is extended to a dual energy source with a plurality of alternating low energy and high energy windows in the detector direction. In other words, a dual energy acquisition is illustrated in FIG. 20 with an isofan detector geometry at a single projection view (i.e., at angle $\beta$). The dual energy filter is located at or near the source creating low and high energy data alternated in the detector channel direction ($\delta$-axis). In some embodiments, the dual energy filter is positioned closer to the source than to an opposing detector. A sinogram representation (cartesian coordinates) of the acquired dual energy data form a single revolution $(0 \leq \beta \leq 2\pi)$ is illustrated in FIG. 21. Specifically, for every X-ray projection below the solid dividing line at $\beta=\pi-2\delta$, there is a conjugate X-ray above the line. For example, similarly dashed type (e.g., heavy dash, thin dash) lines in FIG. 21 are conjugate samples. Similar to the process described in FIGS. 17A-17C, FIGS. 22A and 22B illustrate the data filing scheme using conjugate X-ray principle for the low and high energy data. Solid shaded regions are physically acquired low energy and high energy data, whereas patterned or hashed regions are physically acquired data sampled at a later view angle.

Figure 22A:
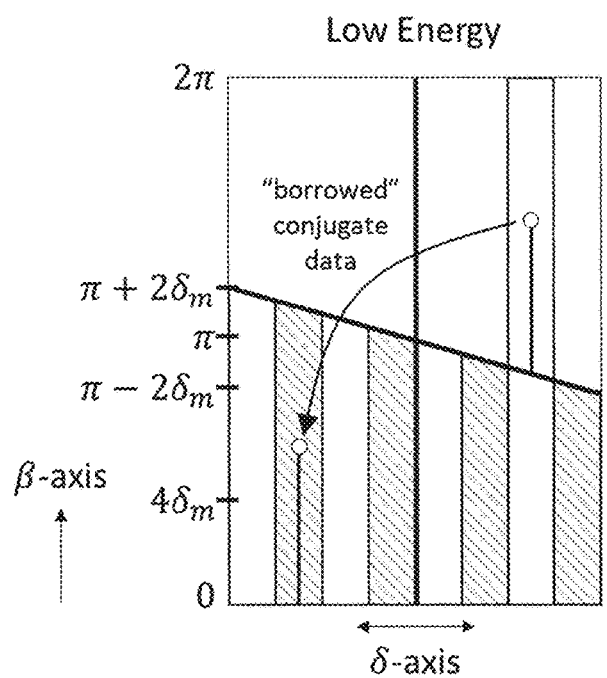
FIG. 22A is a sinogram for low energy reconstruction including both native and conjugate samples.
Figure 22B:
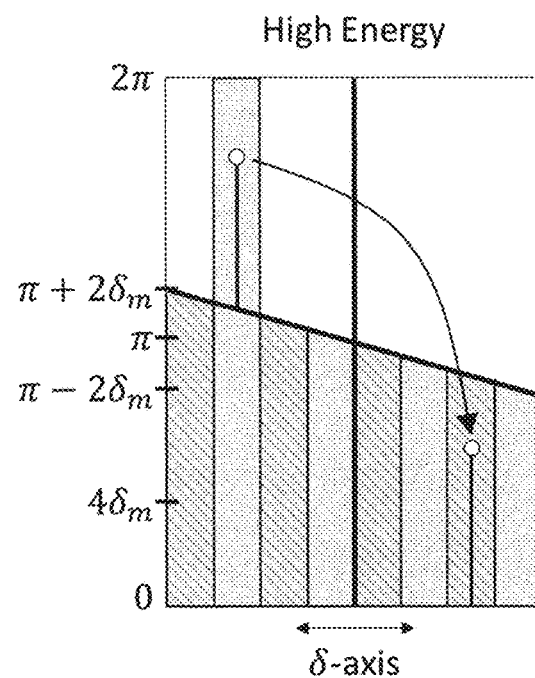
FIG. 22B is a sinogram for high energy reconstruction including both native and conjugate samples.

Using the reconstruction method described herein, the dual energy scan can reconstruct a low energy image and a high energy image by utilizing the conjugacy shown in FIGS. 21, 22A, and 22B. In some embodiments, the temporal resolution of the conjugate data filing scheme is proportional to $\beta_2-\beta_1=\pi+2\gamma_1$.

In some embodiments, the data completion module utilizes high order interpolation to fill in the data across the block of detector channels corresponding to the other energy. With reference to FIG. 27, an embodiment the high order interpolation is illustrated, which is used to complete the signal for the low energy and high energy data sets. Interpolation via a weighting scheme for the data across detector columns forms a continuous same energy signal in a given projection view. The projection views that are displaced in time (e.g., 1 time sample later, 1 time sample earlier) have increasing errors that are proportional both to the time difference and the distance from the isocenter.

In some embodiments, the data completion module utilized machine learning to provide interpolation across the energy gaps within a given view. Each block of detector channels encodes information about the attenuation coefficient at a different energy, thereby enabling one to obtain a continuous same energy signal.

In some embodiments, the machine learning includes a convoluted neural network (CNN), a U-Net architecture, and/or a generative adversarial network (GAN). For example, the machine learning network can use a T (number of β samples)×U (number of δ or γ samples)×V (number of detector rows) sinogram image (natively acquired) as input and output two T×U/2×V sinograms for each energy level. These two sinograms are then passed to the image reconstruction algorithm to produce two N (number of image pixels in x or y)×N×M (number of image pixels in z) image volumes.

A machine learning network that learns the interpolation is one that has the same input and output dimensions (a raw-to-raw correction network). This is different than a network that directly learns how to reconstruct the image, which is a network that takes sinogram input (T×U×V) and outputs two N×N×M images. In other embodiments, the machine learning network includes an image-to-image network where native data is reconstructed once, then a single N×N×M image is passed to convolutional neural network and output one or two N×N×M images. Image-to-image networks can be used as an artifact correction method.

In some embodiments, the data completion module utilizes iterative reconstruction (IR) algorithms. In some embodiments, the iterative reconstruction algorithms based on sparse sampling (e.g., compressed sensing) can also use the native discontinuous signal measurements within each view without necessarily having to perform a data completion for a continuous signal. Therefore, low and high energy images can be obtained using iterative reconstruction algorithms with only the native data as an input; achieving the theoretically highest spatial and temporal resolution possible between images.

In some embodiments, the data completion module utilizes any one of data conjugacy, high order interpolation, machine learning, and/or iterative reconstruction to improve the resolution of the dual energy CT images. In some embodiments, the data competition module utilizes any combination of data conjugacy, high order interpolation, machine learning, and iterative reconstruction.

Each of the reconstruction schemes mentioned herein are applicable to helical acquisition. In some embodiment, the X-ray source is translated along the rotational axis (z-axis) relative to a stationary subject or patient. Samples in the conjugate or high order interpolation data completion modules therefore have a z-dependence associated with them. As such, the data inconsistency associated with the z-dependence for the purposes of data completion may lead to image artifacts. The severity of these artifacts increases with increasing translation speed of the X-ray source (i.e., increasing helical pitch, increasing z direction speed). However, below a threshold speed, these artifacts are not sufficiently present to adversely affect image quality. In some embodiments, the threshold speed is a function of the end use of the imaging (e.g., treatment planning diagnostic radiology, etc.) In some embodiments, various artifact correction methods are utilized to increase the threshold speed. For example, an image-to-image machine learning network is utilized in some embodiments to correct artifacts.

Conventional CT image reconstruction algorithms are based on two fundamental assumptions: 1) that the object remains the same throughout the entire scan, and 2) that you have a continuous set of measurements of the object in every view. Convention CT hardware components are designed in accordance with both assumptions.

In single energy data acquisition, the CT scanner satisfies both assumptions. The first assumption is met (assuming no object motion) and the object's material properties (e.g., the photon attenuation coefficient) are the same for a given energy probe. The second assumption is also met by having a continuous set of detectors to measure the signal opposite the X-ray source.

In dual energy data acquisition, conventional scanners are designed to satisfy both fundamental assumptions. Specifically, conventional dual energy CT hardware had a continuous signal in every view because the detector channels for a given view are probed with the same energy spectrum. In contrast, the CT scanner 100 has alternating signals of low and high energy along the detector channel dimension, which is contrary to the second fundamental assumption. The low and high energy signals in any given projection view are no longer continuous. As presented herein, the systems and methods described provide algorithmic correction to obtain a continuous signal in every view (or to use the discontinuous signal directly) for dual energy image reconstruction.

With reference to FIGS. 23A-23C, a simulation of CT acquisitions in sinogram form for low energy (FIG. 23A), high energy (FIG. 23B) and dual energy (FIG. 23C) are illustrated. The dual energy CT acquisitions have alternating electromagnetic spectral attenuation along the detector channel direction. In the illustrated simulation, the dual energy filter included 17 low energy bands (window or columns) and 17 high energy bands (windows or columns) for a total of 34 alternating bands.

With reference to FIG. 24, image reconstruction from the simulated CT sinograms of FIGS. 23A-23C is illustrated. FIG. 24(a) illustrates the high energy (e.g., 85 kV) reference and FIG. 24(b) illustrates the low energy (e.g., 65 kV) reference used for simulation. FIG. 24(c) illustrate the single energy acquisition reconstruction for high energy and FIG. 24(d) illustrates the single energy acquisition reconstruction for low energy. FIG. 24(e) illustrates an uncorrected high energy image for a dual energy acquisition utilizing the conjugate date filing scheme described herein. Likewise, FIG. 24(f) illustrates an uncorrected low energy image for a dual energy acquisition utilizing the conjugate data filing scheme described herein. FIGS. 24(*g*) and 24(*h*) are corrected versions (e.g., artifacts removed) of FIGS. 24(*e*) and 24(*f*), respectively. In some embodiments, the artifacts are removed by smoothing the binary weights pictured in FIG. 15B. For example, smoothing the binary weights includes in some embodiments a Gaussian filter over FIG. 15B. In other words, the hard edge in FIG. 15B leads to the image streaks seen in FIGS. 24(*e*) and 24(*f*). The systems and methods described herein provide several advantages. One advantage is the detector arrays are centered on the rotational axis while oriented to the focal spot, which provides a wide fan angle. In some embodiments, the field of view is approximately 62 cm. This detector arrangement also provides higher photon fluence at the edges than conventional arrangements centered on a focal spot. See FIG. 12.

Another advantage is the dual energy filter is positioned at or near the source, which provides improved spectral separation. In addition, positioning the dual energy filter at or near the source prevents non-imaging flux from reaching the patient.

Another advantage is that view sampling runs at twice the frame rate. Every other column (or alternating groups of columns) collects two complete data sets in a single rotation.

Another advantage is the dual energy reconstruction method provides a maximized temporal resolution for dual energy acquisition. Also, different frames of reference can be utilized to create two complete low energy and high energy data sets. Missing low energy or high energy data can be filled in or completed using a conjugate method, interpolation, machine learning, etc.

As such, the dual energy CT scanner described herein provides increased spatial and temporal resolution over conventional designs by splitting the X-ray spectra at the source along the detector channel dimension and using filter materials (e.g., Au and Mo) chosen to increase the energy and contrast resolution of the acquisition. Also, the CT scanner provides full sampling of the low and high energy data sets required for image reconstruction.

Methods

In some embodiments, the technology provides methods for obtaining a medical image (e.g., a CT scan, a magnetic resonance imaging (MRI) scan, a positron emission tomography (PET) scan, a single-photon emission computerized tomography (SPECT) scan, a photon counting computed tomography scan, or a portal image or scanogram (e.g., scanned projection radiography image). While exemplary methods are described for obtaining a CT scan, the technology is not limited to methods for obtaining a CT scan and includes embodiments for obtaining other types of medical images.

In some embodiments, a CT scan is performed by the following steps: (1) the patient is positioned in the patient positioning device; (2) the gantry tilt angle is adjusted to match the patient's spine angle; (3) the CT ring is positioned around the patient and positioning device; (4) scans are acquired with a source operated at approximately 140 kVp (in other embodiments, the source is operated within a range of approximate 10 kVp to approximately 200 kVp); (5) an appropriate filter is inserted in the 140 kVp X-ray beam path to yield given spectra: first material (e.g., gold) low energy, second material (e.g., molybdenum) high energy, and alternating first and second material windows (e.g., dual energy); (6) the CT ring scans the desired patient window.

In some embodiments, methods comprise providing a patient positioning system to hold a patient in a vertical position (e.g., seated, seated and leaning backward, seated and leaning forward, standing, standing and leaning backward, standing and leaning forward, kneeling, kneeling and leaning forward, or kneeling and leaning backward, or other vertical or substantially vertical position). See, e.g., Int'l Pat. App. Pub. No. WO 2019/056055 and U.S. Pat. App. Pub. No. 2020/0268327, each of which is incorporated herein by reference.

Figure 28:
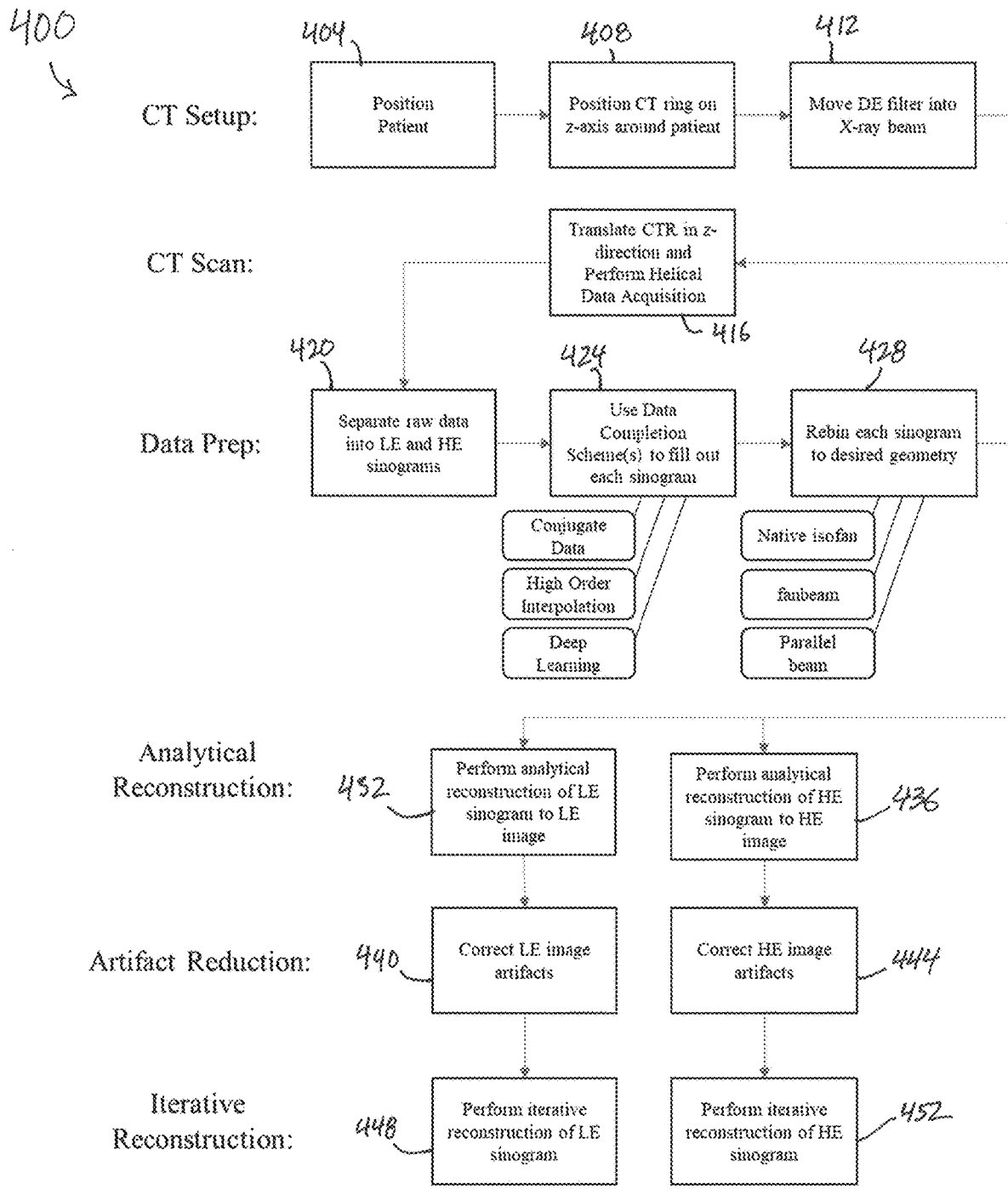
FIG. 28 is a method of dual energy image reconstruction.

In some embodiments, e.g., as shown in FIG. 28, a method 400 of obtaining and creating a CT image is illustrated. The method 400 in the illustrated embodiment is divided into a CT setup phase, a CT scan phase, a data preparation phase, an analytical reconstruction phase, an artifact reduction phase, and an iterative reconstruction phase.

With continued reference to FIG. 28, the CT setup phase of the method 400 includes positioning a patient relative to the CT scanner (STEP 404), positioning the CT scanner ring on a z-axis around the patient (STEP 408), and moving the dual energy filter into the X-ray beam (STEP 412).

The CT scan phase of the method 400 includes translating the CT ring in the z-direction while rotating a source and at least one detector about an axis (STEP 416). In some embodiments, the source and the at least one detector translate along the axis while simultaneously rotating about the axis (helical acquisition). The at least one detector is configured to detect an output from the source (e.g., the detectors measure the X-ray attenuation). The STEP 416 also includes recording an output signal from the at least one detector as sampled data. In other words, the detector output signal is sampled at a given time to provide a detector sample associated with that time period. In some embodiments, the sampled data is stored on memory, a network, or other suitable data storage solution.

The data preparation phase of the method 400 includes separating the sampled data into a first data set and a second data set (STEP 420) (separate raw data into low and high energy sinograms). The method 400 includes completing the first data set with a data completion module to create a first full data set and completing the second data set with the data completion module to create a second full data set (STEP 424). As described herein, the data completion module in some embodiments utilized conjugate data to create a full data set. In other embodiments, the data completion module utilizes a high order interpolation. In other embodiments, the data completion module utilizes a machine learning method. In other embodiments, the data completion module utilizes any combination of data completion schemes described herein. In some embodiments, the first data set and/or the second data set are transformed (rebinned) from a first geometric frame of reference (e.g., native isocenter) to a second geometric frame of reference (e.g., fanbeam or parallel) (STEP 428).

With continued reference to FIG. 28, the method 400 includes reconstructing a first CT image with the full first data set (STEP 432) and reconstructing a second CT image with the full second data set (STEP 436) (analytical reconstruction phase). The method 400 further includes, in some embodiments, correction of image artifacts in the low energy image and the high energy image is performed utilizing any number of suitable artifact reduction techniques (STEP 440 and STEP 444) (artifact reduction phase).

With continued reference to FIG. 28, in some embodiments, the method 400 includes an iterative reconstruction phase that includes iterating on reconstructing the first CT image (STEP 448). In some embodiments, the method 400 further includes iterating on reconstructing the second CT image (STEP 452).

In some embodiments, methods comprise obtaining (e.g., acquiring, recording, etc.) a medical image. In some embodiments, comprise obtaining (e.g., acquiring, recording, etc.) a CT image, MRI image, PET image, SPECT image, photon counting computed tomography image, or a portal image or scanned projection radiography image (e.g., "scout" scan). In some embodiments, methods comprise activating an imaging source (e.g., electromagnetic radiation source, X-ray source, gamma ray source, radio wave source, photon source, proton source, positron source, gamma ray source (e.g., gamma rays from a positron source)). In some embodiments, methods comprise activating an imaging detector (e.g., electromagnetic radiation detector, X-ray detector, photon detector, gamma ray detector), e.g., detecting electromagnetic radiation, X-rays, gamma rays, radio waves, photons, protons, positrons, etc. using the detector.

In some embodiments relating to CT scanning methods, methods comprise generating X-rays using an X-ray generator of the scanner ring. In some embodiments, methods comprise detecting X-rays using an X-ray detector of the scanner ring. In some embodiments, methods comprise revolving an X-ray generator and an opposed X-ray detector around the patient. In some embodiments, methods comprise revolving an X-ray generator and an opposed X-ray detector around the patient while the scanner ring is stationary with respect to the gantry arms. In some embodiments, methods comprise revolving an X-ray generator and an opposed X-ray detector around the patient while the scanner ring moves with respect to the gantry arms.

Systems

The technology provides embodiments of systems. For example, the technology provides multi-axis medical imaging systems. In some embodiments, the medical imaging system is a computerized tomography (CT) system, a magnetic resonance imaging (MRI) system, a positron emission tomography (PET) system, a single-photon emission computerized tomography (SPECT) system, a photon counting computed tomography system, or a portal imaging system or scanned projection radiography imaging system. While the technology is described for exemplary embodiments wherein the medical imaging system is a computerized tomography (CT) system, the technology is not limited to a CT scanning system and embodiments are to be understood to include other types of medical imaging systems.

In some embodiments, systems comprise a multi-axis medical imaging apparatus as described herein and software components and/or hardware components structured to rotate the gantry and/or to translate the scanner ring. In some embodiments, systems comprise software components structured to perform a method as described herein. In some embodiments, systems comprise a multi-axis medical imaging apparatus, software for obtaining (e.g., recording, acquiring) a medical image, and software for controlling gantry rotation and scanner ring translation.

In some embodiments, systems comprise a multi-axis medical imaging apparatus as described herein and a controller. In some embodiments, the medical imaging source and detector communicate with the controller. In some embodiments, the controller activates the medical imaging source and collects the image projections from the detector. In some embodiments, the controller controls movement of the medical imaging source and detector in opposition around the scanner ring. In some embodiments, the controller communicates with a camera (e.g., a horizontal camera and/or a vertical camera) positioned to obtain an elevational image and/or a plan image of a region occupied by a patient. In some embodiments, the controller communicates with a graphic display terminal for providing output images such as tomographic images, positioning information, and user input devices such as a keyboard for receiving instructions from a user. In some embodiments, the controller has a general computer architecture including one or more processors communicating with a memory for the storage of non-transient control programs (e.g., to store tomographic projection sets and resulting tomographic images).

In some embodiments, systems comprise a multi-axis medical imaging apparatus comprising one or more cameras (e.g., a scanner ring comprising one or more cameras). In some embodiments, the cameras record images that are subsequently processed by software (e.g., configured to perform image recording, image analysis, image storage, image manipulation, and/or image comparison methods) and/or hardware components (e.g., microprocessors, graphics processors, communications buses configured to communicate, record, analyze, store, manipulate, and/or compare images) of the imaging subsystem.

In some embodiments, systems comprise a multi-axis CT scanner as described herein and software components and/or hardware components structured to rotate the gantry and/or to translate the scanner ring. In some embodiments, systems comprise software components structured to perform a method as described herein.

In some embodiments, systems comprise a multi-axis CT scanner, software for obtaining (e.g., recording, acquiring) a CT scan, and software for controlling gantry rotation and scanner ring translation.

In some embodiments, systems comprise a multi-axis CT scanner as described herein, a patient in an upright (e.g., vertical (e.g., substantially and/or essentially vertical position)), and a user who interacts with controls structured to move the multi-axis CT scanner and acquire CT scans of said patient or a portion thereof.

Some portions of this description describe the embodiments of the technology in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times to refer to these arrangements of operations as modules, without loss of generality. The described operations and their associated modules may be embodied in software, firmware, hardware, or any combinations thereof.

Certain steps, operations, or processes described herein may be performed or implemented with one or more hardware or software modules, alone or in combination with other devices. In some embodiments, a software module is implemented with a computer program product comprising a computer-readable medium containing computer program code, which can be executed by a computer processor for performing any or all steps, operations, or processes described.

In some embodiments, systems comprise a computer and/or data storage provided virtually (e.g., as a cloud computing resource). In particular embodiments, the technology comprises use of cloud computing to provide a virtual computer system that comprises the components and/or performs the functions of a computer as described herein. Thus, in some embodiments, cloud computing provides infrastructure, applications, and software as described herein through a network and/or over the internet. In some embodiments, computing resources (e.g., data analysis, calculation, data storage, application programs, file storage, etc.) are remotely provided over a network (e.g., the internet).

Embodiments of the technology may also relate to an apparatus for performing the operations herein. This apparatus may be specially constructed for the required purposes and/or it may comprise a general-purpose computing device selectively activated or reconfigured by a computer program stored in the computer. Such a computer program may be stored in a non-transitory, tangible computer readable storage medium or any type of media suitable for storing electronic instructions, which may be coupled to a computer system bus. Furthermore, any computing systems referred to in the specification may include a single processor or may be architectures employing multiple processor designs for increased computing capability.

In some embodiments, the technology (e.g., a system) comprises an image reconstruction component (e.g., a hardware component and/or a software component) within the scanner ring and the image reconstruction component is configured to produce (e.g., reconstruct) medical images, e.g., from raw data (e.g., from raw image data). In some embodiments, the technology (e.g., a system) comprises a data transfer component that communicates raw image data acquired by the scanner ring (e.g., acquired by a detector of the scanner ring) to a component configured to produce (e.g., reconstruct) medical images. In some embodiments, the scanner ring comprises the data transfer component and the component configured to produce (e.g., reconstruct) medical images is separate from the medical imaging apparatus (e.g., a computer connected to the medical imaging apparatus by a wired and/or wireless communications component).

USES

In some embodiments, the technology provided herein finds use in medical, clinical, and research settings. For example, in some embodiments, the technology finds use in imaging a biological system, e.g., an organism (e.g., an animal, a human), organ, tissue, and/or cell. In some embodiments, the technology finds use in imaging a head, neck, lungs, heart, circulatory system (e.g., arteries and/or veins), abdomen, pelvic region, gastrointestinal system, axial skeleton (e.g., spine), kidneys, and/or extremities. For example, in some embodiments, the technology finds use in diagnosing and/or treating a disease and/or injury. For example, the technology finds use in preventive medicine, disease screening, disease diagnosis, disease treatment, and/or disease monitoring. For example, in some embodiments, the technology finds use in diagnosing and/or treating a cancer. In some embodiments, the technology finds use in imaging the chest, e.g., for diagnosis of pneumothorax, emphysema, cardiomegaly, fibrosis, diaphragmatic hernias, empyema, atelectasis, pneumonia, pulmonary edema, pulmonary hemorrhage, primary lung malignancy, or a metastatic disease. In some embodiments, the technology finds use in diagnosing and/or treating a calcification, bone trauma, hemorrhage, edema, infarction, and/or tumor. The technology also finds use in research settings, e.g., to image an animal, human, organ, or tissue for research uses. The technology also finds use in veterinary medical settings, e.g., to image an animal, organ, or tissue for diagnosis and/or treatment. In some embodiments, the technology finds use in industrial uses, e.g., to image a non-biological object, e.g., to identify characteristics of construction, material defects, internal contents, etc., without breaking or otherwise disrupting the non-biological object.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A computerized tomography (CT) scanner comprising:
a source defining an imaging plane; and
a filter including a first filter portion including a first material, a second filter portion including a second material, and a third filter portion including the first material and the second material;
wherein the third filter portion includes alternating columns of the first material and the second material, wherein each column intersects the imaging plane; and
wherein the filter is movable with respect to the source to align any one of the first filter portion, the second filter portion, and the third filter portion with the imaging plane.

2. The scanner of claim 1, wherein the first material attenuates an X-ray spectrum a first amount; and wherein the second material attenuates the X-ray spectrum a second amount, different than the first amount.

3. The scanner of claim 1, wherein the first material has a first mass attenuation coefficient within a range of 0.1 cm$^2$/g to 200 cm$^2$/g corresponding to an excitation within a range of 10 to 200 kV$_p$, and the second material has a second mass attenuation coefficient corresponding to the excitation different than the first mass attenuation coefficient.

4. The scanner of claim 1, wherein the first material is gold, and wherein the second material is molybdenum.

5. The scanner of claim 1, wherein the first material is gold, and wherein the second material is tin.

6. The scanner of claim 1, wherein the third filter portion is positioned between the first filter portion and the second filter portion.

7. The scanner of claim 1, wherein the filter defines a radius.

8. The scanner of claim 1, further including a filter adjustment assembly with a motor, a frame, and a linkage coupled between the motor and the frame, wherein the filter is coupled to the frame.

9. The scanner of claim 1, wherein the first filter portion at least partially overlaps the third filter portion, and the second filter portion at least partially overlaps the third filter portion.

10. A computerized tomography (CT) scanner comprising:
a source defining an imaging plane; and
a filter including a first filter portion including a first material, a second filter portion including a second material, and a third filter portion including the first material and the second material;

wherein the first material has a first mass attenuation coefficient within a range of 0.1 cm$^2$/g to 200 cm$^2$/g corresponding to an excitation within a range of 10 to 200 kV$_p$, and the second material has a second mass attenuation coefficient corresponding to the excitation different than the first mass attenuation coefficient; and wherein the filter is movable with respect to the source to align any one of the first filter portion, the second filter portion, and the third filter portion with the imaging plane.

11. The scanner of claim 10, wherein the first material is gold, and wherein the second material is molybdenum or tin.

12. The scanner of claim 10, wherein the third filter portion is positioned between the first filter portion and the second filter portion.

13. The scanner of claim 10, wherein the first filter portion at least partially overlaps the third filter portion, and the second filter portion at least partially overlaps the third filter portion.

14. A computerized tomography (CT) scanner comprising:
   a source defining an imaging plane; and
   a filter including a first filter portion including a first material, a second filter portion including a second material, and a third filter portion including the first material and the second material;
   wherein the first material is gold, and wherein the second material is molybdenum; and
   wherein the filter is movable with respect to the source to align any one of the first filter portion, the second filter portion, and the third filter portion with the imaging plane.

15. The scanner of claim 14, wherein the third filter portion is positioned between the first filter portion and the second filter portion.

16. The scanner of claim 14, wherein the first filter portion at least partially overlaps the third filter portion, and the second filter portion at least partially overlaps the third filter portion.

17. A computerized tomography (CT) scanner comprising:
   a source defining an imaging plane; and
   a filter including a first filter portion including a first material, a second filter portion including a second material, and a third filter portion including the first material and the second material;
   wherein the first material is gold, and wherein the second material is tin; and
   wherein the filter is movable with respect to the source to align any one of the first filter portion, the second filter portion, and the third filter portion with the imaging plane.

18. The scanner of claim 17, wherein the third filter portion is positioned between the first filter portion and the second filter portion.

19. The scanner of claim 17, wherein the first filter portion at least partially overlaps the third filter portion, and the second filter portion at least partially overlaps the third filter portion.

20. A computerized tomography (CT) scanner comprising:
   a source defining an imaging plane; and
   a filter including a first filter portion including a first material, a second filter portion including a second material, and a third filter portion including the first material and the second material;
   wherein the third filter portion is positioned between the first filter portion and the second filter portion; and
   wherein the filter is movable with respect to the source to align any one of the first filter portion, the second filter portion, and the third filter portion with the imaging plane.

21. The scanner of claim 20, wherein the third filter portion includes alternating columns of the first material and the second material, wherein each column intersects the imaging plane.

22. The scanner of claim 21, wherein the first material is gold, and wherein the second material is molybdenum or tin.

23. A computerized tomography (CT) scanner comprising:
   a source defining an imaging plane; and
   a filter including a first filter portion including a first material, a second filter portion including a second material, and a third filter portion including the first material and the second material;
   wherein the first filter portion at least partially overlaps the third filter portion, and the second filter portion at least partially overlaps the third filter portion; and
   wherein the filter is movable with respect to the source to align any one of the first filter portion, the second filter portion, and the third filter portion with the imaging plane.

24. The scanner of claim 21, wherein the first material is gold, and wherein the second material is molybdenum or tin.

* * * * *